United States Patent
Glace et al.

(12) 
(10) Patent No.: US 6,331,291 B1
(45) Date of Patent: *Dec. 18, 2001

(54) DENTIFRICE GEL/PASTE COMPOSITIONS

(76) Inventors: William R. Glace, 225 Soares, Orcutt, CA (US) 93455; Robert L. Ibsen, 1571 E. Main St., Santa Maria, CA (US) 93454; George A. Skoler, 6 Carriage Way, White Plains, NY (US) 10605

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/856,606

(22) Filed: May 15, 1997

Related U.S. Application Data

(60) Provisional application No. 60/051,874, filed on May 30, 1996.

(51) Int. Cl.[7] ................. A61K 7/16; A61K 5/00; A61K 7/20
(52) U.S. Cl. ................. 424/49; 424/52; 424/50; 424/53; 433/215
(58) Field of Search ................. 433/215; 424/49, 424/50, 52, 53

(56) References Cited

U.S. PATENT DOCUMENTS

| | | | | |
|---|---|---|---|---|
| 3,547,413 | * | 12/1970 | Rosenthol | 424/81 |
| 4,376,006 | * | 3/1983 | Fischer | 433/215 |
| 4,687,519 | * | 8/1987 | Trzasko et al. | 106/211 |
| 4,721,655 | * | 1/1988 | Trzasko et al. | 428/530 |
| 4,986,981 | * | 1/1991 | Glace et al. | 424/50 |
| 5,041,280 | * | 8/1991 | Smigel | 424/52 |
| 5,084,268 | * | 1/1992 | Thaler | 424/53 |
| 5,098,303 | * | 3/1992 | Fischer | 433/215 |
| 5,302,374 | * | 4/1994 | Wagner | 424/49 |
| 5,386,405 | * | 1/1995 | Rennie et al. | 252/174.17 |

* cited by examiner

*Primary Examiner*—James H. Reamer

(57) ABSTRACT

A thixotropic, smooth-flowing liquid, bulk-water-free dentifrice gel/paste that contains a stable mixture of at least one of amylopectin containing discrete solid particles and modified amylopectin containing discrete solid particles, uniformly suspended in and wetted by an inert essentially anhydrous organic hydroxylated liquid matrix material, and which dentifrice gel/paste is characterized by a high surface sheen. Preferably, the modified homopolysaccharide discrete particles contain esterified amylopectin and/or esterified amylose. The dentifrice gel/paste can be used as a toothpaste, a bleaching gel and a brushing gel.

38 Claims, No Drawings

DENTIFRICE GEL/PASTE COMPOSITIONS

RELATED APPLICATION

This application claims the benefit of the filing date of copending provisional application Ser. No. 60/051,874, filed May 30, 1996.

BRIEF DESCRIPTION OF THE INVENTION

A water-free (i.e., excluding intentionally-added water) creamy dental gel/paste product having the characteristics of a gel and a paste that contains a stable heterogeneous mixture of an essentially anhydrous organic polyol, a large quantity of amylopectin or a modified amylopectin and one or more thickening agents.

BACKGROUND TO THE INVENTION

Toothpaste, brushing gel and bleaching gel utilize a blended matrix material into which is provided a detergent, whiteners, plaque and/or tartar removers or inhibitors, flavorings, viscosity control agents, fluoridizers and the like. No particular toothpaste matrix material is utilized for a brushing gel or a bleaching gel. In most toothpastes and brushing and bleaching gel formulations, water is a critical component of the blended matrix material. Toothpastes come in various viscosities and their flow characteristics fluctuate depending on whether the paste is thixotropic or not. There is a paucity of information about the relative viscosities of toothpastes, the film forming qualities of dentifrices (pastes and gels), and the importance of such to the utility of the product. However, Fischer, U.S. Pat. No. 5,098,303; U.S. Pat. No. 5, 234,342 and U.S. Pat. No. 5,376,006, teach that the viscosity characteristics of a bleaching gel should be different from the viscosity characteristics of a brushing gel and takes the position that bleaching gels must possess extremely high viscosities in order to stick to the teeth during a bleaching period. To accomplish this, Fischer describes excessively high viscosity (e.g., >500,000 centipoises) water-based gels using high carbomer gelling agent concentrations (3.5 weight percent or greater).

A dentifrice may bring to the gums and teeth certain ingredients that affect gums and teeth. They include fluorides, hydrogen peroxide, enzymes, and special gum treatment agents. The respective utilities of such additives dependent on their residence time in contact with the gums and tooth enamel. The longer such additives remain in contact with the gum and teeth, that is, the longer the residence time in contact with the gums and tooth enamel, one can assume that they better contribute their special qualities. A dentifrice that disintegrates once it is brushed or otherwise exposed to the tooth and gum surfaces provides the minimum residence time. A dentifrice that does not readily disintegrate at the tooth and gum surfaces provides a higher residence time. The latter dentifrice can be expected to contribute more of the benefits to the teeth and gums of the additives in the dentifrice formulation.

Every dentifrice has some film forming qualities when applied to teeth and gums. The longer the dentifrice maintains a film while applied over the teeth and gums, the longer is the aforementioned residence time. Dentifrices that are water based typically form films on the teeth and gum that quickly disintegrate once the film is exposed to water (water added by the user or saliva carried to the tooth and gum surface). Water is an excellent solvent for a water-based dentifrice. Consequently, water-based dentifrices have relatively short residence times.

There are two basic fluid dental cleansing compositions marketed today. They are dental pastes (i.e., toothpastes) and dental gels (brushing gels and bleaching gels). Each is dispensed through a tubular orifice to the user's tooth brushing device or, in the case of some bleaching gels, to the user's dental tray (bleaching tray, stint or mouthguard). An important quality of a dental cleansing composition is its flow characteristics as it issues from the tubular orifice. If the composition is runny as it issues to and from the orifice, it is difficult to control the amount of composition to be applied to the brushing device or dental tray. If the composition is too viscous, then it is difficult to expel to and from the orifice and consequentially, the amount of composition to be applied to the brushing device or dental tray is difficult to control.

However, if the composition is neither runny nor too viscous but is unnecessarily sticky, it leaves a stringy tail as a blob issues from the orifice. When the tail separates from the orifice opening it falls to many places that the users wishes it would not, such on the brushing device handle and other non-brush head surfaces, or when deposited into a dental tray, over the tray's edges onto whatever surface exists outside of the tray. The flow characteristics of such compositions in the tube are also affected by the flow characteristics of the composition. If the composition is runny, it is more difficult to expel from the tube, but once it reaches the orifice opening, it is difficult to control its issuance from the tube's orifice. If the composition is too viscous, it is difficult o force it to the issuing orifice, and difficult to expel it from the orifice. If the composition is too sticky, it is extremely difficult to control the amount of composition that issues from the orifice because the stringy tail invariably causes more to issue than the user desires, or less to issue than the user desires, because the user is attempting to anticipate the extra amount issuing due to the composition's stickiness. There is another adverse flow category that involves neither runny, too viscous, nor sticky compositions; this flow has the appearance of a dry (non-glossy) mass while issuing from the orifice. The problem with such compositions is that the mass does not cleave well from the orifice, sometimes taking a few efforts of asserting the brush head or dental tray against the mass in order to dislodge it from the orifice. Frequently, when such composition is dislodged from the orifice, it fails to lie comfortably on the brush head or the dental tray. In the case of extrusion into a dental tray, such materials are difficult to distribute about the tray to assure uniformly distributed contact with the teeth.

On the whole, toothpastes are easier to formulate to control flow characteristics because they rely to a significant extent on simple filler loading to control flow. Dental gels, on the other hand, rely on the complex chemical interaction of a gelling aid to hydrogen bond with a matrix component of the dental gel formulation. Such chemical interaction is difficult to control in order to fine-tune the flow characteristics of the dental gel.

Dental gels are vehicles for dentifrices, bleaching aids and fluoride compounds. Gels are colloids in which the dispersed phase has combined with the dispersion medium to produce a semisolid material, such as a jelly. They are typically characterized as sticky, viscous liquids that have poor spreadability as their viscosity increases. This stickiness is sometimes averted in water-based gels by the addition of fillers that do not interfere with the water-white qualities of the gel.

Dental gels are used as a dental paste (toothpaste) substitute, as brushing gels that contain peroxide and as whitening gels that contain peroxide. The toothpaste substitute and the brushing gels are used with a toothbrush whereas the whitening gel is deposited in a dental tray and placed repeatedly over the patients teeth for extended periods of times, ranging from 30 minutes to 8 hours. Whitening is effected by the bleaching action derived from the oxygen generated by decomposition of the peroxide. A stable peroxide that fails to properly decompose provides no whitening oxygen, whereas a prematurely decomposed peroxide is ineffective because the bleaching oxygen is removed before the whitening treatment of the patient's teeth.

A dental paste (toothpaste) is a dentifrice that is in the form of a soft, smooth, thick mixture containing a filler material, typically in an aqueous liquid vehicle, that gives the mixture flow characteristics. A dental paste exhibits little of the chemical interactions that take place in forming a dental gel. Illustrative of a most desirable dental paste is found in Glace et al., U.S. Pat. No. 4,986,981, patented Jan. 22, 1991, and assigned to Den-Mat Corporation. It covers the whitener formulation that is used in Rembrandt® toothpaste. This patent describes enhanced whitening of teeth using in the formulation the combination of citrates and a proteolytic enzyme such as papain. Browning et al., in *Journal of Dental Research,* 1994, vol. 73, article 1774, compare proteolytic enzymes to hydrogen peroxide, and found them to be comparable as teeth whitening agents.

Dental gels depend on a dispersion medium that combines with a gelling aid. There are a number of effective gelling aids used in forming dental gels. One class of gelling aid is the carbomer, which is a class of high molecular weight polymers based on acrylic acid crosslinked with allyl sucrose. The carbomers provide high yield values and thus are very effective suspending agents. The carbomers have extremely high molecular weights ranging from about 700,000 to about 5,000,000. B. F. Goodrich Specialty Chemicals sell them under the Carbopol® name. Other gelling aids are nonionic surfactants. Another category of gelling aid is polyethylene oxide macro-polymers such as Polymer H™ sold by Union Carbide Chemicals and Plastics Co., Inc.

The dispersion medium are polar compositions that effectively hydrogen bond with the gelling aid. A conventional and highly efficient dispersion medium is water. Another is glycerine. Frequently, a mixture of these two dispersion mediums is employed. The dispersion mediums frequently serve to hydrogen bond with the gelling aids and such generates the gel condition. Fischer, supra, uses a mixture of water and glycerine. A composition sold under the trademark Proxi-Gel® comprises a non-aqueous mixture of glycerine, Carbopol® 940 and carbamide peroxide (denoted herein "a Rosenthal-type gel" because the composition is described by Rosenthal et al., U.S. Pat. No. 3,657,413).

There are a few factors that adversely affect the performance of such dental gels. For example, they do not maintain their viscosity over time. Some of these dental gels are susceptible to viscosity increases and some to viscosity losses, without apparent scientific basis for either event occurring. Such a formulation may start out sticky and viscous, but with time, the formulation can significantly lose such properties. he second is that such gels are capable of levels of interbonding that when the products are squeezed from tubes and syringes, they leave a long stringy tacky residue emanating from the tube and syringe opening. Such residue deposit the gel in undesired places such as in a patient's mouth (as distinguished from the patient's teeth), on the users hands, on equipment such as a toothbrush handle, and the like.

In investigating such gels, it has been noted that in relatively homogeneous systems in which the gelling aid combines principally with a low molecular weight dispersion medium such as water, the gels possess the adverse qualities noted above.

A "Rosenthal-type gel" also suffers from such poor flow characteristics. That investigation has led to the conclusion that a desirable dental gel is one that possesses a thick creamy consistency as contrasted with a thick curdy consistency. In addition, the thick creamy composition should have the ability to extrude from an orifice, such as a tube or syringe, opening without the stringiness noted in prior art gel formulations. The term "creamy" is a characterization that is not effectively employed with the dental gels of the prior art. Contrary to what has been achieved in the prior art, it would be desirable to create a dental gel product that possesses a smooth, thick creamy texture and flow characteristic, without the undesirable stringiness, and retains its flow (Theological) characteristics after manufacture, for an extended period of time. Most importantly, the dentifrice gel should form a film on teeth and gums that is thick and somewhat resistant to disintegration by water. It should be tacky enough to bond to enamel and have such film integrity that when contacted by water, it dissolves slowly enough so that it has a sufficient residence time on teeth and gums to provide maximum benefits from the additives in the composition.

It has been determined that a desirable dental gel is one in which the gelling aid operates in a heterogeneous environment. That is to say, the gelling aid is hydrogen bonded to at least two distinctly different matrix components in the formulation, one being liquid and the other comprising a wettable particulate solid. A preferred system is one in which an active particle is suspended in and wetted by a non-aqueous low molecular weight dispersion medium. Water is so active in hydrogen bonding the gelling aid and as a wetting agent for the particulate solid that it causes the particles to strongly interbond through the gelling aid, inducing in some formulations the curdy appearance. An active particle is characterized as a finely divided solid that possesses surface groups that are amenable to wetting by the non-aqueous low molecular weight medium.

Thaler, in U.S. Pat. Nos. 5,084,268 and 5,208,010, describes an abrasive free hydrogen peroxide tooth whitening dentifrice that is a blend under high speed mixing, of cornstarch, sorbitol, Carbopol® 940, flavor, sodium lauryl sulfate, sodium saccharin, potassium sorbate, and sodium benzoate in water, to which in a final step, hydrogen peroxide is added. The depicted formulations contain from about 30 to about 61.25 weight percent of water. Of significance, the formulation depicted in the patents fails to contain fluoride and this may be because of the perceived reactivity of fluorides with peroxides. Cornstarch is aggressively wetted by water and, as such, functions as a gelling aid. It serves the function in the formulation as the material that causes gelation by hydrogen bonding with other components of the formulation, particularly water. Water dissolves sorbitol. Thus sorbitol will not function as the dispersion medium in the formulations of these patents. It functions as a humectant and sweetening agent. Cornstarch, in a later addition to the formulation, is indicated by Thaler to function as a filler at that stage. Carbopol® 940 is well known to form water based gels. Hydrogen peroxide is added at the last stage of the formulation after the temperature of the formulation is cooled to 30° C. The composition is defined as having a toothpaste consistency.

A commercial product that is allegedly based on these patents is called "Booster", sold by Dental Concepts Inc., Elmsford, N.Y. 10523. Booster is described as a product that is not to be used alone. It is to be used in conjunction with the user's regular toothpaste. In this regard, reference is made to Wagner, U.S. Pat. No. 5,302,374, which describes the combination of the Thaler patent product with a conventional toothpaste. When Booster dries, it leaves a crusty product. In addition, Booster, when squeezed from its tube, is a relatively low light reflecting gel suggesting that the particulate cornstarch component extends to the surface of the extruded mass, as a filler, and cuts down the light reflectance of the liquid components in the formulation. Though Booster has the white appearance of cream, it is curdy and not creamy in the way it flows, and as a result, it does the opposite of stringiness by converting the curdy mass into more coagulated lumps when deposited on a surface.

However, rubbing of the curdy mass on a surface, causes the formation of a thin smooth transparent film that possesses a slight tackiness that is quickly disintegrated by water. It is easily wiped from the surface with light rubbing with a tissue. However, when Booster is spread on paper as a film, the water in the composition is readily absorbed into the paper and out of the composition, to form in a short while, a dry-to-touch flat coating.

The general consensus in the dental profession is that a bleaching gel that relies on carbamide peroxide for whitening has to have available water that allows the chemical reaction that releases hydrogen peroxide as an oxidizing agent, in which case it is reduced to water, for bleaching teeth. The decomposition of the peroxide may be induced by the presence of the enzyme catalase.[1] The reaction is

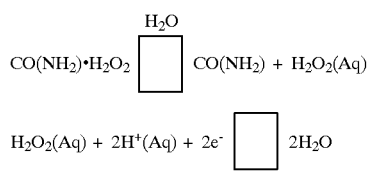

[1] An enzyme of the oxidoreductase class found in the blood and in most living cells that catalyzes the decomposition of hydrogen peroxide into water and oxygen, thereby protecting cells.

According to Hawley's Condensed Chemical Dictionary, Twelfth Edition, Van Nostrand Reinhold Company, N.Y. (1993), carbamide peroxide (urea peroxide) is decomposed by moisture at temperatures around 40° C. Its active oxygen content is minimally 16 weight percent.

Starches are reserve polysaccharides in plants, such as corn. potatoes, tapioca, rice, and wheat. They are composed of about 20–40 weight percent of amylose and 60–80 weight percent of amylopectin. For example, cornstarch is a specific starch that is composed of about 20–25% amylose and about 75–80% amylopectin. Amylopectin is a branched homopolysaccharide version of the amylose homopolysaccharide. Cornstarch is a white powder that swells in water. It is the most widely used starch in the U.S. The chief uses for starches are as adhesives, machine-coated paper, textile filler and sizing agent, beater additive in papermaking, gelling agent and thickener in food products, oil well drilling fluids, filler in baking powders, fabric stiffener in laundering, urea-formaldehyde resin adhesives for particle board and fiberboard, explosives, dextrin, chelating and sequestering agent in foods, indicator in analytical chemistry, anti-caking agent in sugar, face powders, abherent and mold-release agent, polymer base, and the like. Some starches contain more amylose than other starches, but for all practical purposes, amylopectin is the dominant, on a weight basis, component of the composition of starches.

Amylose and amylopectin are classified as homopolysaccharides. Amylopectin has the following repeating unit structure:

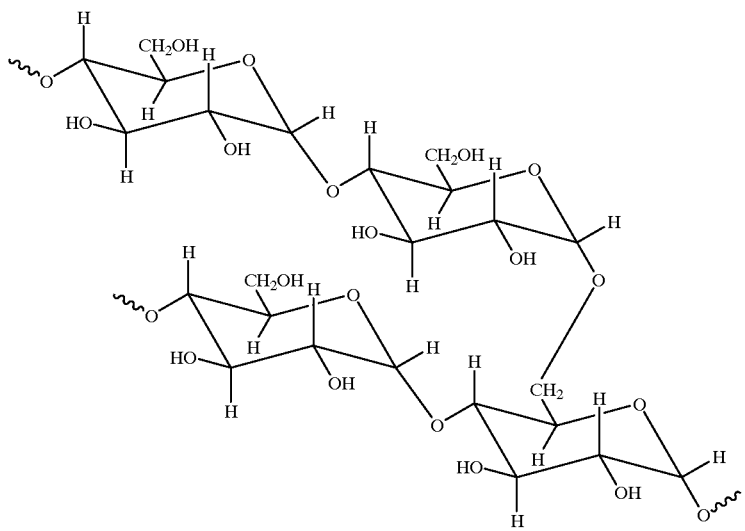

Amylose is a homopolymer of the following repeating unit structure:

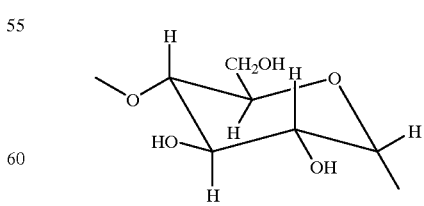

These polymers have molecular weights in the range of about 150,000 to about 600,000 (Morrison and Boyd, *Organic Chemistry*, Fifth Edition, 1987, p. 1333).

It is well known to acylate amylopectin and amylose. Acylation is commonly carried out by reacting amylopectin and/or amylose with an organic carboxylic acid or anhydride in the presence of an acid or basic catalyst. A preferred form of acylated amylopectin and amylose is the acetylated version formed by reacting acetic acid or anhydride with amylopectin and/or amylose in the presence of an acid or base catalyst, such as the mineral acids, e.g., sulfuric acid, hydrochloric acid, phosphoric acid, and the like, or an organic sulfonic acid such as Armstrong's acid, toluene sulfonic acid, triflic acid, or Friedel-Crafts catalysts, or in the presence of a basic catalyst, such as an alkali metal hydroxide, e.g., NaOH, KOH, and the like. Another preferred form of acylating amylopectin or amylose is the reaction of these carbohydrates with a dicarboxylic acid, preferably an aliphatic dicarboxylic acid, such as protecting cells. malonic acid, maleic acid or anhydride, succinic acid, adipic acid, or mixed anhydrides of such acids. For example, a mixed dianhydride of adipic acid and acetic acid can be reacted in the presence of a strong mineral acid or the strong organic acids, or a strong base such as the alkali metal hydroxides, with amylopectin and/or amylose to form the acetate and adipate of amylopectin and/or amylose.

Mooney et al., U.S. Pat. No. 5,085,228, patented Feb. 4, 1992, describe the use of a modified starch as an adhesive in cigarette manufacture. The starch compositions of Mooney et al. involve a mixture of modified starches that have an amylopectin content of at least 70%, an preferably at least 75%, by weight. Starches that are contemplated include waxy maize, waxy rice, tapioca, potato, maize (corn), wheat, arrowroot and sago. Of these, Mooney et al. prefer waxy and root starches, especially waxy maize, tapioca and potato. The mixed starch comprises a crosslinked starch with fluidity or converted starch and derivatives thereof. The crosslinked starch is obtained by treating a conventional starch with a multifunctional reagent. Suitable crosslinking agents include mixed anhydrides of acetic and di- or tribasic acids, epichlorohydrin, phosphorous oxychloride, sodium metaphosphate and di- or polyepoxides with the mixed anhydrides being preferred. According to Mooney et al., the degree of crosslinking may vary depending on the desired properties and conditions of cooking with light and moderate crosslinking typically being applied. Generally, this means crosslinking with up to about 1.0% of a reagent based on the weight of the starch, preferably up to about 0.2% and more preferably up to about 0.1%. According to Mooney et al., crosslinking can vary from about 0.005 to 1% by weight of reagent based on the weight of starch and preferably from 0.005% to 0.2%, more preferably from about 0.01 to 0.1%.

The fluidity of converted starches are typically starches which are acid converted, although other chemical conversions such as enyzyme conversion and oxidation may also be used. These starches are generally identified by their fluidity or WF (water fluidity) number which is an inverse viscosity measurement of measure of the degree of degradation of the starch. The higher the fluidity number (WF), the more degraded the starch and the thinner the viscosity. Mooney et al., define WF and described information on obtaining acid-converted starches, at column 3, lines 5–18.

Analogous procedures for acylating amylopectin and amylose is described in U.S. Pat. Nos. 4,721,655 and 4,687,519, which in their examples demonstrate the acylation of these saccharides by way of reaction with an anhydride.

National Starch and Chemical Company, Food Products Division, Bridgewater, N.J. sell a preferred form of such a reaction product as Colflo 67. Colflo 67 is a white to off-white powdery solid, acetylated essentially 100% amylopectin adipate with a molecular weight greater than 10,000, that possesses the following properties: a pH of ~6 in a 1% aqueous solution, a specific gravity of 1.5, 87% total carbohydrates and a bound moisture content of about 8–12%. The structure of Colflo 67 is believed to be equivalent to the following formula.

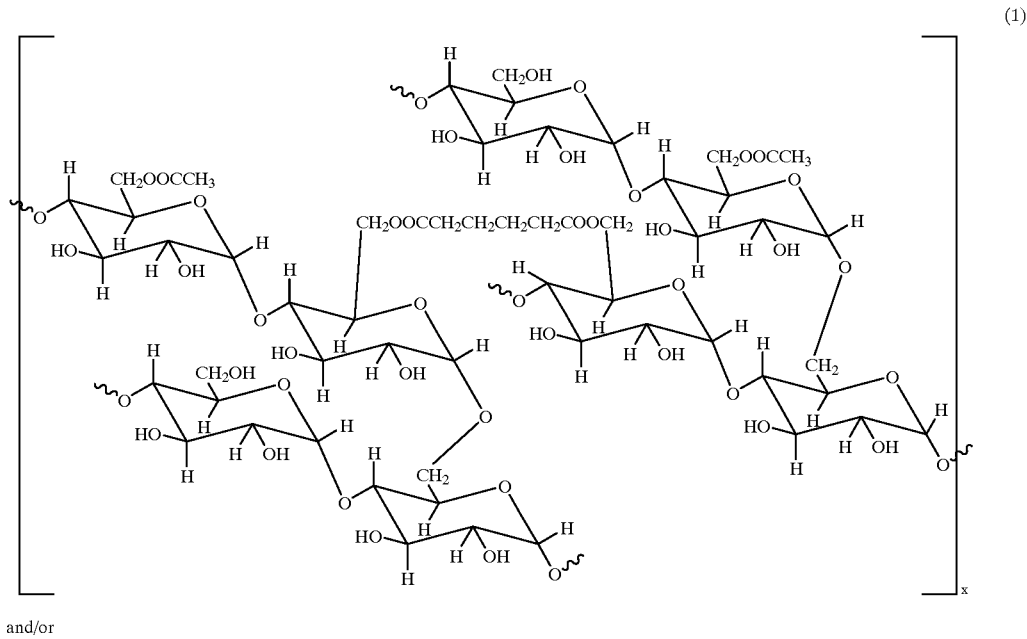

and/or

-continued

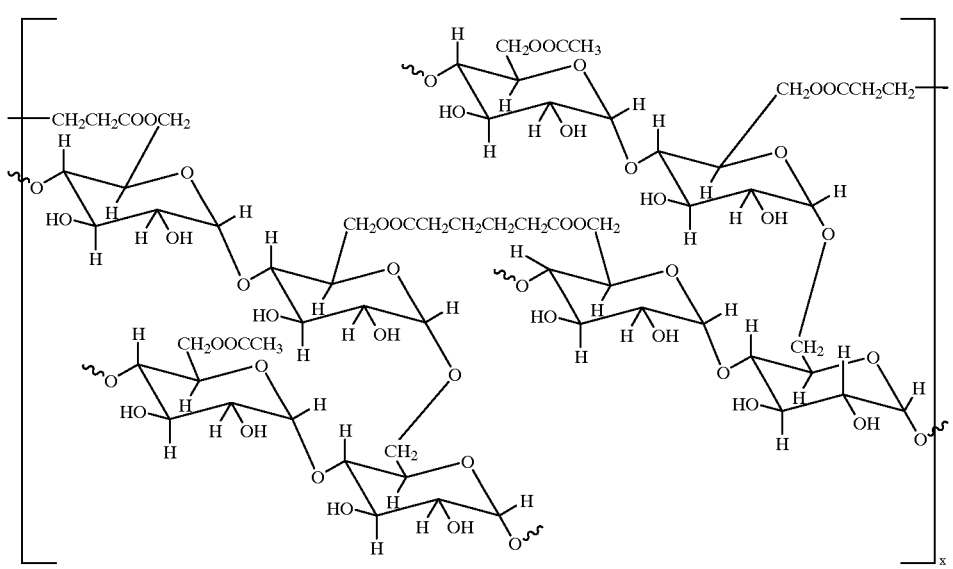

(2)

More of the hydroxy groups may be acetylated resulting in the following structures:

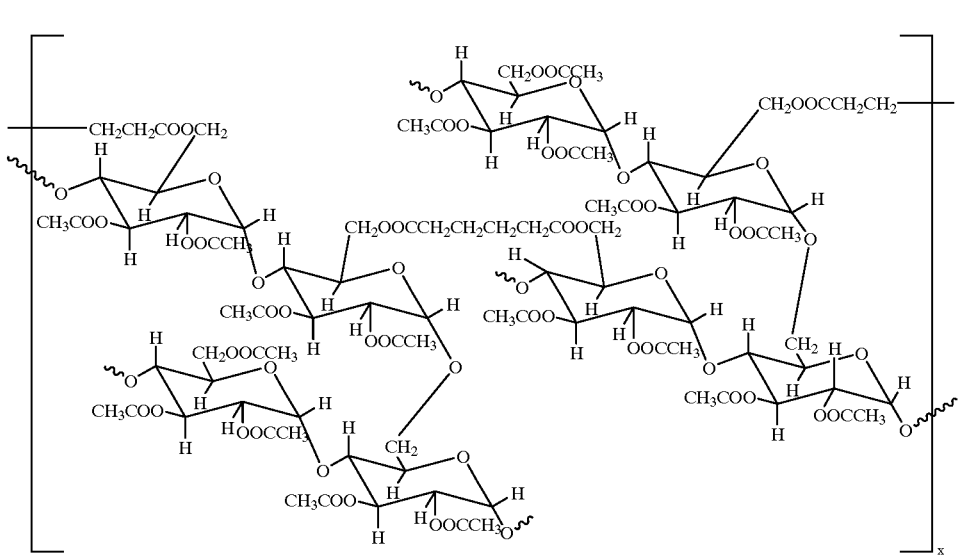

(3)

The above acylated amylopectin are preferred structures in the practice of this invention.

It would not seem possible to use such acylated amylopectin or even non-acylated amylopectin to make an effective water-free dentifrice in view of the fact that when propylene glycol is mixed with either of them, on standing overnight at room temperature, the mixture solidifies to an apparently intractable mass. However, the same is not true when bulk water is added to amylopectin or acylated amylopectin. The resulting water containing mixture forms a fluid pasty mass, from which on standing, the amylopectin or acylated amylopectin separates but can be reformed into the paste by mixing. Starches are conventionally mixed with bulk water, i.e., a distinct mass or portion of water,[2] to form a useful product such as a paste. However, when the water-laden paste is dried, there is formed a crusty brittle solid. In addition, a body of such aqueous starch mixtures possesses a rather non-glossy surface indicating that the starch particles are not fully covered by a liquid reflective layer.

[2] For example, water that is contained in a container before it is mixed with another material.

According to Thaler, supra, starch is a gelling agent for water, even in the presence of carbomer gelling agent. Amylopectin and acylated amylopectin do not function as a gelling agent for polyols and the combination solidifies as noted above. Thus, the vehicle in which the amylopectin or the acylated amylopectin is mixed is critical to their performances. Acylated amylopectin is different from the starch from which it is derived. For example, Colflo 67 is derived from waxy maize and possess properties considerably distinctive from waxy maize.

The dentifrice gel/paste of the invention bears none of the characteristics noted above for mixtures of amylopectin or acylated amylopectin with polyols. The dentifrice gel/paste of the invention is a stable flowable creamy composition that possesses extremely desirable dentifrice properties.

THE INVENTION

This invention relates to dentifrice[3] gel/paste possessing the following properties:

[3] The term "dentifrice" is intended to encompass the broadest dictionary meaning of a substance for cleaning teeth, and is not intended to be limited by any definition used by the U.S. Food and Drug Administration.

1. the dentifrice gel/paste is a smooth flowing liquid gel in which homopolysaccharide and/or a modified homopolysaccharide particles are suspended in and wetted by a non-aqueous low molecular weight dispersion matrix for the gel;
2. the dentifrice gel/paste is thixotropic;
3. the dentifrice gel/paste exhibits, without modification, a high surface sheen (i.e., it possesses a high surface gloss);
4. the dentifrice gel/paste is relatively water-free because it is free of intentionally-added bulk water;
5. the dentifrice gel/paste is a stable homogenized multiphase stable mixture of homopolysaccharide, and/or modified homopolysaccharide particles containing esterified amylopectin and/or esterified amylose, uniformly dispersed in an inert essentially anhydrous organic hydroxylated liquid matrix material functioning as the non-aqueous low molecular weight dispersion matrix;
6. the dentifrice gel/paste forms a sticky and tacky film on teeth that withstands nonaqueous rubbing with a toothbrush, but which will incrementally disperse on contact with water and saliva;
7. the dentifrice gel/paste is extrudable from a tube or syringe orifice opening as a stable creamy fluid having an uniform viscosity, that is cleanly (without forming a sticky mess on any surface, such as the orifice opening, a patients hands, brush handle, dental tray, and the like) cleaved like soft, non-fluid butter, and neatly deposited on the toothbrush bristles or into a dental tray;
8. the dentifrice gel/paste hold flavoring additives in a unique manner because the flavoring is more intense to taste when formulated in the dentifrice gel/paste of the invention (particularly so when the amylopectin in the formulation is a modified amylopectin) than in a conventional toothpaste or gel, and to the extent that the flavoring allows, the flavoring from the dentifrice gel/paste of the invention penetrates gum tissue to leave a clean flavor on the gums hours after brushing, the effect one obtains from a quality mouthwash, thus leaving the user with a mouth-wash-fresh clean feeling;
9. the dentifrice gel/paste in the preferred formulation, using modified homopolysaccharide particles, gives an unique cleansing sensation, in that after brushing with this preferred formulation, the users teeth have a slippery-clean feel when one rubs the upper incisors with ones upper lip, as contrasted with a typical prior art formulation that leaves a gritty-feeling residue on the teeth; and
10. the dentifrice gel/paste of the invention maintains its creamy flowable viscosity over extended periods of time, even when heated at temperatures as high as 40° C. (104° F.).

The surface of the dentifrice gel/paste of the invention exhibits glistening brightness and luster indicating that the dispersed solid components in the dentifrice gel/paste are coated by a distinct liquid phase (or layer) that contributes a sheen to the product. Microscopic evaluation of the dentifrice gel/paste of the invention shows that it a heterogeneous uniform mixture of at least two phases, one phase being a liquid continuous phase comprising the essentially anhydrous organic hydroxylated liquid matrix material in the formulation, and another phase comprising fine particulates in which the amylopectin component of the formulation is dominant.

The dentifrice gel/paste of the invention is characterized by a stable viscous creamy texture when extruded from a tube or syringe orifice, and when deposited on a surface, the mass retains the creamy characteristic. However, when a body of the dentifrice gel of the invention is spread over a solid surface, it forms a glistening and tacky white-opaque (in a system to which no pigmentation or colorant is added) film that significantly bonds to the surface, and is not easily wiped away from the surface. As a result, the dentifrice gel/paste of the invention will cling to teeth enamel surfaces in the absence of added water and/or saliva. When the same formulation of the invention is modified by the substitution of a substantial amount of water, substituting for up to 50% of the essentially anhydrous organic hydroxylated liquid matrix material component, the surface of the gel/paste loses its shine and a coated film of the resultant gel/paste is relatively dull in appearance, and the film does not bond as uniformly and as tightly as the dentifrice gel/paste of the invention.

The expression "relatively water-free" is intended to encompass a product in which water is not intentionally added in bulk form but water may be present as molecular water that is bound to any of the materials that are used in formulating the dentifrice gel/paste of the invention. The molecular water that is bound to the amylopectin or the modified amylopectin additive used in the dentifrice gel/paste of the invention can be readily removed by heating the additive at moderate temperatures below that which degrades the amylopectin or the modified amylopectin additive. Whether such bound water is present or removed plays an insignificant role in the performance of the dentifrice gel/paste of the invention.

The dentifrice gel/paste formulation of the invention, as indicated above, also contains an essentially anhydrous organic hydroxylated liquid matrix material. The preferred organic hydroxylated liquid matrix material is one or more liquids which remain liquid at temperatures as low as about 0° C., or lower, to as high as about 290° C., or higher, as determined at atmospheric pressure. Illustrative of such organic hydroxylated liquid matrix materials, are one or more aliphatic organic polyols, e.g., glycerine and propylene glycols of the formula:

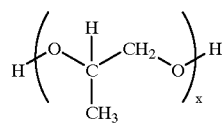

wherein x has a value of 1 to about 5. The use of glycerine alone and mixtures of glycerine and 1,2-propylene glycol are preferred organic hydroxylated liquid matrix materials in accordance with this invention. The term "essentially anhydrous" means that the polyol is free of added bulk water. Such polyols are typically hygroscopic which means that on standing in a normal atmosphere, they will absorb water. The water that is absorbed will seldom exceed about 1–2 percent of the polyols weight.

In addition, the dentifrice formulation of the invention includes a small quantity of a high molecular weight acidic polymer such as a carboxylated polymer and/or silica, which have the capacity to hydrogen bond with the aliphatic organic polyols to create the gel structure.

Preferably, this invention relates to a stable homogenized essentially-anhydrous gel/paste derived from a limited quantity of granulated, finely and uniformly dispersed, esterified amylopectin and/or esterified amylose with a relatively small amount of a powdered carbomer polymer, both in an essentially anhydrous hydroxylated organic liquid matrix material that wets each component and allows the formation of the gelled state. It is preferred that the amount of modified homopolysaccharide by weight in the dentifrice gel exceeds the weight amount of the carbomer polymer, and the weight amount of the matrix material exceeds the weight of both the modified homopolysaccharide and the carbomer polymer. This dentifrice gel per se possesses cleansing properties of a dentifrice. In the preferred form, the smooth textured dentifrice gel product of the invention contains at least one other active ingredient that contributes to the dentifrice's performance, either as a whitener, brightener, fluorider, and the like.

Contrary to conventional dental gels, which are water-white clear gels—that is, they approach water in colorlessness and clarity, in bulk and film form—the smooth textured water-free dentifrice gel/pastes of this invention are opaque both in bulk and in thin film form. However, the thinner the film is made, the more translucent it becomes. Food grade pigmentation (colorant) can be added to the gel formulation to either make the gel whiter, or another color. Particulate materials that reflect light, such as fish scales, ground mica, and the like, can be added to the formulation to enhance the visual attractiveness of the extruded dentifrice.

The smooth flowing thixotropic, high sheen (glossy), relatively water-free multiphase dentifrice gel products of the invention have viscosities ranging from about 50,000 to about 200,000 centipoises when measured at 23.5° C. on a Brookfield Viscometer, Model DV-II, spindle 6, at 10 rpm's. However, preferred viscosities of the dentifrice's of the invention are in the range of about 65,000 to about 180,000, more preferably, in the range of about 75,000 to about 150,000, centipoises when measured at 23.5° C.

An important property of the dentifrice gels of the invention is thixotropy.[4] Thixotropy is important to the performance and flow characteristics of the dentifrice of the invention. A thixotropic gel/paste of the invention has good flow characteristics when pressure is applied to it, and a non-runny consistency when it is at rest, as it is when it is deposited on a toothbrush or a dental tray. In addition, a thixotropic gel/paste can be exuded with pressure from the tube orifice and retain the gel/paste consistency throughout, without dripping. When the user has exuded by pressure the amount of gel/paste that the user desires to employ, the user merely has to wipe the orifice opening across the brush head or across an edge of the dental tray to cut of the desired amount of the gel/paste from the orifice opening. Alternatively, the brush head or dental tray edge may be wiped against the orifice opening to cut off the desired amount of the gel/paste. Because the gel/paste of the invention is thixotropic, it easily and cleanly cuts from the orifice opening as if a sharpened knife-edge=is slice through the gel/paste.

[4]"The ability of certain colloidal gels to liquefy when agitated (as by shaking or ultrasonic vibration) and to return to the gel form when at rest. This is observed in some clays, paints, and printing inks which flow freely on application of slight pressure, as by brushing or rolling. Suspension of bentonite clay in water display this property, which is desirable in oil-well drilling fluids." Hawley's Condensed Chemical Dictionary, Twelfth Edition, revised by Richard J. Lewis, Sr.

Thixotropy provides other benefits. The thixotropic gel/paste of the invention meters itself in the brushing operation so that it is uniformly distributed to the area of teeth to which it is applied. If the brushing action is slow, the gel/paste of the invention resides as a relatively thick film on the surface to which is applied. As the brushing action is accelerated, the film is distributed as a thick froth to the brushing area. Eventually, the brushing action whisks the last remnants of the film into the froth that cleanses and polishes the teeth surface. Thus, if the gel/paste of the invention possesses the whiteners and plaque and tartar removers described in U.S. Pat. No. 4,986,981, supra, such reside at the tooth surface longer resulting in more effective application of these components to the teeth.

The advantages of thixotropy are particularly applicable in whitening teeth with hydrogen peroxide through use of carbamide peroxide. The gel/paste of the invention lends itself to easy and effective distribution into a dental tray that is to be worn by a patient during the day or at night. Because the gel/paste formulation of the invention without colorant added, is naturally white, when it is placed in a clear plastic dental tray molded to a configuration of the teeth, it does not per se adversely affect the appearance of the patient, particularly if the tray is to be worn during waking hour activities. A tray that is filled with a proper dosage of the gel/paste can be fitted over the teeth to be whitened, as described in the prior art. The thixotropic gel/paste of the invention conveniently and neatly moves about the teeth surfaces, and when the tray is at rest, the gel/paste thickens and adheres to the teeth. This adherence of the film allows the peroxide, if in adduct form, to become separated via enzymatic action and then decomposed by enzymatic action to form active oxidizing oxygen that whitens and treats gum surfaces, thereby minimizing plaque, tartar and gum infections (e.g., gingivitis).

Because the gel/paste of the invention has natural tackiness, even though it has a much lower viscosity than other whitening gels, it tightly adheres to the teeth being treated. This is caused by the viscoelastic relationship between the essentially anhydrous organic polyol, the amylopectin component and the thickening or gelling agent. Since it contains no added water, it is not in a diluted state and when water is introduced to the tray through saliva action, the ptyalin[5] in the saliva causes catalytic attack of the gel/paste resulting in incremental breakdown of the gel/paste film over the teeth. This introduces a mild exotherm that facilitates the enzymatic action on the hydrogen peroxide cleaved from the carbamide peroxide. Consequently, it is believed that the concomitant breakdown of the film and the peroxide component therein results in more effective peroxide action on the teeth, with consequent enhancement of teeth whitening and gum protection from gingivitis.

[5]A form of amylase in the saliva of human beings and some animals that catalyzes the hydrolysis of starch into maltose and dextrin.

One distinction between this dentifrice from other dentifrices is the fact that it is an essentially anhydrous composition. It is anhydrous in that essentially no free water is added to the formulation. Any water in the formulation is bound water, i.e., water that is chemically bound to one of the ingredients in the formulation. For example, the homopolysaccharide and/or the modified homopolysaccharide may contain from about 0 to about 15 weight percent bound water, that is, water that is hydrogen bonded to the modified homopolysaccharide structure. The hydroxylated liquid matrix material may be hygroscopic, and absorb water on standing. Such water is bound to the matrix material's chemical structure. For example, glycerine, a preferred hydroxylated liquid matrix material, is hygroscopic and will absorb water on standing. However, the amounts of water in the formulation based on bound water will not, in any case, exceed about 5 weight percent of the weight of the dentifrice formulation.

A further embodiment of this invention resides in the use of a combination of whiteners, which when combined in the dentifrice gel/paste of this invention, provides a synergistic improvement in whitening over that obtainable from each of the whiteners when used alone as the sole whitener in the formulation. This invention combines in the formulation, a combination of one or more enzymes and hydrogen peroxide, either as hydrogen peroxide per se, hydrogen peroxide coupled with another molecule such as urea, or a compound that decomposes or one, or more compounds that decompose, to form hydrogen peroxide during use of the dentifrice. The preferred enzymes are one or more enzymes of the general classes, such as, lyase, isomerase, ligase, oxidoreductase, transferase and hydrolase. Specific illustrations of most desirable enzymes are the proteolytic enzymes such as papain, bromelain (bromelin)[6] and ficin (ficain).[7] Other suitable enzymes[8] include protease, dextranase, lipase, neutral protease, oxidoreductase and actinidin (derived from kiwi). Evaluations of this combination of whiteners demonstrate that the combination of these whiteners, especially when citrates are present, achieve superior teeth whitening results.

[6]Any of several cysteine endopeptidases that catalyze the cleavage of proteins on the carboxyl side of alanine, glycine, lysine, and tyrosine bonds. Differing forms are derived from the fruit (fruit bromelain) and stem (stem bromelain) of the pineapple plant, ananas comosus.

[7]An enzyme of the hydrolase class that catalyzes the cleavage of proteins on the carboxyl side of lysine, alanine, tyrosine, glycine, asparagine, leucine, and valine bonds. It is a cysteine endopeptidase derived from the sap of fig trees. Because it enhances the agglutination of red blood cells with IgG antibodies, it is used in the determination of the Rh factor; it is also used as a protein digestant in a variety of industrial applications.

[8]See the following U.S. Pat. Nos. 4,154,815; 4,140,758; 3,981,989; 4,082,841; 3,696,191; 5,094,840; 4,871,532; and 4,466,954.

DETAILED DESCRIPTION OF THE INVENTION

This invention provides for a formulation that can be used as a dentifrice gel/paste (e.g., toothpaste), a bleaching gel and a brushing gel, and the only material difference between such classes of products is the amount of peroxide and/or proteolytic enzyme that is provided in the formulation. In the case of a dentifrice gel/paste, the formulation may contain from 0 to about 3.5 weight percent of theoretically available hydrogen peroxide. In the case of a brushing gel, the formulation may contain from about 0.5 to 20 weight percent of theoretically available hydrogen peroxide. In the case of a bleaching gel, the formulation may contain from about 1 to about 25 weight percent of theoretically available hydrogen peroxide. The provision of proteolytic enzyme in such formulations typically enhances the peroxide whitening performance. In the preferred practice of the invention, the hydrogen peroxide is coupled as carbamide peroxide and used in that form. Since carbamide peroxide contains about 36% of it weight as hydrogen peroxide, a dentifrice that contains 35 weight percent of carbamide peroxide contains about 12.66 percent of theoretically available hydrogen peroxide. When an enzyme is included in the formulation in combination with hydrogen peroxide, whether hydrogen peroxide per se or a compound that generates or provides hydrogen peroxide, it is desirable to employ from 0.1 to 20 parts by weight of the enzyme for each part by weight of hydrogen peroxide.

The preferred form of hydrogen peroxide that is used in the formulations of the invention, when hydrogen peroxide is employed, is carbamide peroxide because it is anhydrous and stable. Calcium peroxide can be used in the formulation of the invention, but it is not a preferred choice for peroxide contribution. Aqueous solutions of hydrogen peroxide are not used in the invention because such includes undesirable concentrations of water, unless the amount of such hydrogen peroxide is low enough and the concentration of water in which the peroxide is dissolved is sufficiently small so that the overall formulation does not contain more water that is provided in a typical bound water containing formulation, as characterized above. Anhydrous hydrogen peroxide is useable so long as one is careful in its handling. An aqueous hydrogen peroxide solution can be dissolved in glycerine and then subjected to thin film water evaporation so as to reduce the water content to below the bound water level and provide a stable hydrogen peroxide composition.

The ability to use the same basic formulation for all three kinds of teeth treating products, i.e., toothpaste, brushing gel and bleaching gel, stems from certain features of the invention. The dentifrice formulation relies on thixotropy of the composition in order to allow multiple uses for the formulation. That thixotropy is accomplished in an non-aqueous based composition which results in thicker coating of the teeth during dental application, whether with a toothbrush or in a dental tray, without the need for high viscosities. Water is such a strong solvent and so polar that it creates extremely strong bonding with the gelling agent, resulting in a more viscous composition. However, because of its strong solvation characteristics, water cuts the thickness of any coating formed with such aqueous gels. For example, a significant change takes place in the product produced when substituting as much as 20 weight percent water in a formulation encompassed by the invention,. The product loses degrees of gloss, smooth flow, comparable levels of thixotropy, adhesion to proteinaceous surfaces, spreadability, and the like considerations. It is believed that a major difference of this invention from the prior art products that use fillers is that in the case of the gel/paste of this invention, the high boiling organic polyol is restrictively absorbed into the amylopectin and/or acylated amylopectin particles so that a substantial amount of it remains as a continuous phase matrix material for the acylated amylopectin.[9] As a result, particle to particle contact is minimized in the

[9]An experiment that demonstrates the level of absorption of polyol into an amylopectin, such as the acylated amylopectin of the invention, involves the admixture of propylene glycol and acylated amylose/amylopectin that contains 44 weight percent propylene glycol. On standing overnight at room temperature, the mass solidified. However, the formulations of those ingredients into a dentifrice gel/paste of the invention, as characterized in the examples, such as toothpaste #18 described below, is stable overnight and for extended periods of time, such as days, months and years. It is believed that in the absence of a gelling agent, the polyols hydrogen bond with the acylated amylose/amylopectin to form a solid product. When the gelling agent is present, it occupies such levels of hydroxyl functionality in the formulations of the invention that it blocks the type of hydrogen bonding that results in solidification. Another view is that the gel formed by the interaction of the gelling agent and the polyol constitutes the continuous phase of the dentifrice composition, and it surrounds each of the solid particles of amylopectin or acylated amylopectin, preventing them from coalescing into a hard mass. formulations of this invention and the high boiling organic polyol acts as a lubricant for the amylopectin and/or acylated amylopectin particles. In the case where water is used as a solvent, it is quickly imbibed by either the acylated or non-acylated amylopectin particles, swelling them so that the mass possesses particle to particle contact. As a result, the mass of swollen particles exhibit high viscosities, low stickiness and low gloss.

Thus, the composition of the invention results in a thick tooth coating as compared to water-based compositions of the prior art. It is this thick coating that resists rapid decomposition by the action of saliva thereby delaying the removal of the dentifrice from the teeth. Consequently, a dentifrice formulation of the invention that contains such active ingredients as fluoride and/or natural enzymes and/or carbamide peroxide, will maintain such active ingredients for a longer period in contact with the teeth, resulting in greater opportunity for plaque and tartar removal, effective fluoridation, polishing, and/or whitening of the teeth.

Starches are known gelling agents when mixed with water. They form thick pastes. The properties of that paste is dependent on the crosslinked nature of the dominant amylopectin component of the starch. If the dominant component were amylose, which is not crosslinked, then the viscosity of the mixture would lose much of its thickness and pastiness and the composition would have a runny consistency. Thus the crosslinked property of amylopectin contributes to the physical and chemical properties of the paste mixture. As fluid as one would visualize a conventional starch, a waxy maize that is 100% amylopectin forms a much thicker aqueous composition, and hence, is less useful, on the whole. All of such characterization changes when starch is mixed only with polyol. As shown below, it hardens on standing which is not a favorable characteristic, but when combined with another gelling agent in combination with the polyol, it form a thixotropic mass that is suitable for use as a dentifrice gel/paste.

This invention is unique from one viewpoint because of the modified amylopectin component of the dentifrice formulation. That modification takes the form of acylation of amylopectin. When amylopectin is acylated, a major modification to its structure and properties takes place. As one thinks of starch as the glue in a water-based adhesive composition, the substitution of further crosslinking organic acyl moieties for hydroxyl moieties surprisingly converts such a composition from a glue into a thick lubricant in an appropriate formulation, and thus it aids in the flow characteristics of the formulation. This invention shows that there are formulations of further crosslinked amylopectin that provides excellent fluidity in gel/paste compositions, especially for dental usage.

In one embodiment of the invention, the dentifrice gel/paste of the invention comprises esterified amylopectin or esterified amylose where the ester groups have the formula:

$$Y_{(n)}—(—O—O—C—)_a—Z—COO—X \quad (4)$$

wherein X is the residue of amylopectin or amylose, and is embodied by a carbon atom thereof bonded to the "X"-adjacent oxygen, Z is a polyvalent organic moiety containing from 1 to about 16 carbon atoms, preferably a polyvalent hydrocarbon moiety, bonded to at least two carbonyl groups, a and n are numbers having a value of 0 to about 3, Y is hydrogen or an organic moiety, preferably a monovalent organic moiety (and may be inclusive of a residue of amylopectin or amylose), and contains n number of groups to satisfy the free valences of the available—(O—O—C—)—units or the free valence of Z when a is 0. Formula (4) is formed by the reaction of a mixed anhydride of the formula

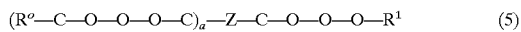

$$(R^o—C—O—O—O—C)_a—Z—C—O—O—O—R^1 \quad (5)$$

with amylopectin and/or amylose under acylation conditions. $R^o$ and $R^1$ are monovalent hydrocarbyl, typically containing 1 to about 9 carbon atoms. Illustrative of such mixed anhydrides are those formed from low molecular weight fatty acids containing 1 to about 10 carbon atoms, such as acetic acid, propionic acid, n-butyric acid, valeric acid, caproic acid, capric acid, isovaleric acid, and the like. These mono-carboxylic organic acids are reacted with aliphatic polycarboxylic acids to form the mixed anhydrides. Suitable aliphatic polycarboxylic acids include oxalic acid, maleic acid, fumaric acid, malonic acid, succinic acid, glutaric acid, α-bromoglutaric acid, β,β-dimethylglutaric acid, adipic acid, 2,5-dimethyl-1,1-cyclopentanedicarboxylic acid, 1,6-cyclohexanedicarboxylic acid, and the like. Preferably, the fatty acids contain from about 2 to about 4 carbon atoms, and the aliphatic polycarboxylic acid contains from 3 to about 8 carbon atoms.

The formation of the mixed anhydrides and their reactions with amylopectin and amylose to form acylated amylopectin and acylated amylose, are thoroughly described in the art, and it is not the intention of this invention to make a novel form of such acylated structures. However, many forms of acylated amylopectin and amylose are contemplated by the prior art even though such may not have been specifically made. To the extent that such modified products are within the purview of the skill in the art, it is the intention of this invention to encompass their use in the compositions, products and methods of this invention.

The principal ingredients of the dental formulations of this invention are the organic polyol, such as glycerine and propylene glycol, the acylated amylopectin, the gelling agent, flavoring, and any active ingredient that treats the teeth. The amount of each of these components of the dentifrice formulation of this invention is not narrowly critical. However, on the whole, the organic polyol comprises from about 20 weight percent to about 65 weight percent of the total weight of the dentifrice formulation. The amylopectin and/or the acylated amylopectin, either as such or in admixture with amylose and/or acylated amylose, comprises from about 5 to about 35 weight percent of the weight of the dentifrice formation. The rest of the formulation comprises the active ingredients, abrasives, surfactant, fillers, enzymes, stabilizers, preservatives, and the like ingredients, provided in amounts that are typically employed in the art.

The gel/paste dentifrice formulations of the invention are of three principal types. One type functions to provide the advantages of a toothpaste, another is to provide the advantages of a brushing or bleaching gel and a third is a formulation that can be used either as a toothpaste, brushing gel or bleaching gel. The brushing and bleaching gels are gel forms of peroxide containing compositions. In the preferred embodiment of this invention, the blushing and bleaching gel also contains enzymes in order to obtain the synergistic cleaning and whitening effect described herein. It would be desirable to possess in one composition the capabilities of an effective whitening or bleaching gel and the capabilities of a dentifrice that resists plaques and tartar formation, while at the same time enhancing the polished look of the teeth.

Plaque is a film of mucus and bacteria on a tooth surface. It comprises living and dead bacteria or bacterial flora, and especially mucopolysaccharides. It may also include various bacterial by-products, some of which are irritating toxins. If sufficient plaque accumulates on teeth and goes down into the crevices between the teeth and the gums, gingivitis may result, and the gums may become swollen and inflamed and tend to bleed easily. If the gums are neglected, periodontitis may develop. As plaque continues to grow between the gums, destroying the periodontal fibers that connect teeth to the bone, it causes pockets where more plaque collects. As periodontal disease progresses, an increasing amount of bone and tissue supporting the teeth are destroyed, and the teeth themselves may be lost, due to lack of support. The bone is lost because of the infection process in the pockets.

As plaque continues to accumulate, it may combine with minerals, particularly calcium in the saliva, to form tartar. Tartar is quite different from plaque, though it has sometimes been called a calcified plaque. Dentists call it calculus. Tartar or calculus is rock hard. It is a white or yellowish deposit. Tartar is largely inert, but controlling tartar also helps to reduce the amount of cleaning to be performed by a dentist. When tartar accumulates below the gum line it can accelerate the progress of periodontal disease, by starting a foreign body reaction in which the body uses the inflammation process to expel the foreign body, which it cannot do since the root is attached to the cementum and the tartar is attached to the root.

An advantage of this invention is that it incorporates the ability of controlling and removing plaque and tartar as described in U.S. Pat. No. 4,986,981, supra, with regular and thorough brushing with a particular formulation of the present invention that incorporates the combination of enzyme, alkali metal citrate and hydrogen peroxide (or optionally calcium peroxide) to aid in preventing the formation of and causing the removal of plaque and calculus while at the same time materially whitening teeth. These ingredients provide no abrasive action, and are preferably used in such proportions as to achieve a slightly acidic to neutral if not actually neutral pH. Because of the inherent acidity of the formulation of this invention, whether involving the gel or paste version of the formulation, citric acid as noted in U.S. Pat. No. 4,986,981, will frequently be an unnecessary ingredient.

This invention takes advantage of the cleaning and biocatalytic capabilities of enzymes. Typically, enzymes function in dilute aqueous solution under moderate conditions of temperature and pH. Because the dentifrice gel/paste of the invention is essentially water free, the enzyme in the formulation is essentially dormant until the dentifrice comes into contact with water (via added water and/or saliva) during the brushing action. Consequently, the full catalytic effect of the enzyme in breaking down the proteinaceous and other materials that accumulate on the teeth is maintained in the formulation and released on the tooth surface at the time of brushing without premature decomposition of the formulation's ingredients. The classes of the enzymes suitable for use in the formulations of the invention include, by way of example, bacterial α-amylases (e.g., glucoamylase, pullulanase, isoamylase, β-amylase, and glucose isomerase), lipases, the oxidoreductases, transferases, hydrolases, lyases, isomerases, and ligases. Any of these classes of suitable enzymes can aid in the cleaning capacity of the formulations of the invention.

As pointed out in U.S. Pat. No. 4,986,981, supra, papain is used in conjunction with the alkali-metal citrate. Papain is an enzyme capable of digesting protein, obtained from the unripe fruit of the papaya and used as a meat tenderizer and in medicine as a digestive aid. Papain, as used herein, refers to the crystalline proteolytic enzyme rather than the crude dried latex. It is prepared from dried papaya latex. According to the Merck Index, the papain molecule consists of one folded polypeptide chain of 212 residues with a molecular weight of about 23,400. It is practically insoluble in most organic solvents, but is somewhat soluble in water or glycerine. Even when used without the citrate, papain has a tendency to dissolve and remove plaque. It is believed that this proteolytic enzyme and the other indicated enzymes, in combination with the hydrogen peroxide, serve to dissolve the proteinaceous matrix of calculus that is attached to dentin and enamel, and attack stains on the enamel. However, the enzymes, when used without the citrate and hydrogen peroxide, have no effect on the calcium content of calculus. When used in conjunction with the citrate and hydrogen peroxide, however, it is able to add to the effectiveness of that material. It has been determined in respect to this invention, a superior cleaning of plaque and tartar is accomplished by the presence in the formulation of hydrogen peroxide. It has been determined that hydrogen peroxide, typically as carbamide peroxide, is very stable when used in the formulations of the invention in combination with enzymes such as papain. It is believed that the water free nature of the formulations of the invention allow enzymes and hydrogen peroxide to reside stably together in the formulation, and to aggressively co-act to attack stains, deposits, plaque and tartar, tooth discoloration, as well as other deposits that form on teeth, to provide a synergistic removal of such. This synergistic co-action occurs when the formulation is mixed with water during the treatment of teeth such as brushing or bleaching in a dental tray.

Preferably, the formulation of the present invention, when employed as a toothpaste, in addition to employing ordinary abrasives, uses a certain amount of small-particle-size aluminum oxide, either hydrated or non-hydrated, but of a type which is small enough in particle size so that there is no scratching of the teeth of dental restorations. The aluminum oxide may be used in conjunction with the typical water insoluble, paste adapted, abrasives used in dentifrices. The abrasive of the toothpaste may be dicalcium phosphate, insoluble sodium metaphosphate, calcium pyrophosphate, calcium orthophosphate, calcium carbonate, magnesium carbonate, or one of a variety of silicates, hydrated and dehydrated silica gels, silica aerogels and xerogels, fumed silica, and the like. Since these agents can differ in their degree of abrasiveness, both between the various types and within each type itself, the abrasiveness is carefully observed and is adjusted to a proper amount which tends to polish teeth, but not to scratch them, whether the teeth are natural teeth, or restorations. These may be included in the formulation in amounts ranging from 0 weight percent up to 60 weight percent, depending on the degree of abrasiveness desired for the formulation, and the abrasivity of the abrasive. A pure bleaching gel desirably is free of such abrasive, while a brushing gel may contain an intermediate amount of such abrasives. A toothpaste formulation may contain from about 20 to 60 weight percent of such abrasives.

Humectants are commonly employed in conventional dentifrices to prevent loss of water from the toothpaste when it is exposed to air. The most frequently such used humectants are sorbitol, glycerine and propylene glycol. Sorbitol and glycerine tend to have a sweet taste. In the practice of this invention, however, polyols such as glycerine are a major component of the matrix of the gel/paste dentifrice of the invention. Since water's presence is not an issue in respect to the drying out of the gel/paste formulation, the polyols are not used in the formulation of the invention to fill the role of a humectant. The polyol function in the formulation of the invention is considerably different from the humectant role in conventional toothpastes and gels.

Thixotropic agents or binders are traditionally added to the water-based dentifrices to help in stabilizing the dentifrice formulation and prevent separation of the liquid from the solid phases. In the practice of this invention, thixotropic agents are used as part of the flow control mechanism of the gel/paste of the invention. The typical thixotropic agents used in toothpaste formulations, such as as natural gums, including gum traganth and gum karaya, the seaweed colloids such as various carageenans, extracts of Irish moss, and sodium alginate, the synthetic celluloses including sodium carboxymethyl cellulose and methyl cellulose, and mineral colloids such as bentonite, are ineffective in forming the gel/paste formulation of this invention. Their presence in the formulation of the invention would not materially affect the flow properties of the gel/paste dentifrice of the invention.

Thixotropy is accomplished according to this invention by the interreaction of the organic polyol component(s), the amylopectin and/or acylated amylopectin component(s) and the gelling agent. The gelling agent is preferably a carbomer, as described above. Illustrative of such carbomers are the Carbopol® water soluble acrylic acid polymers characterized by the following recurring structure:

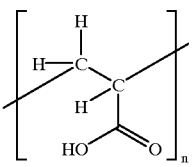

Suitable Carbopol® water soluble acrylic acid polymers include Carbopol® 910, 941, 934, 924P and 940. Carbopol® 934P and 940, because of their abilities to thicken with low concentrations of the polymer, are preferred. These thickening agents are typically used in amounts less than about 1 weight percent of the weight of the dentifrice gel/paste formulation of the invention. However, the amount of the thickener is governed by the viscosity, rheology and thixotropy of the resulting formulation, and thus, the amount of the thickener should be coordinated with the amount of the organic polyol component and the amount of the amylopectin component to achieve the desired viscosity as set forth above and assure the thixotropic flow qualities of the formulation. On the whole, the formulation will employ more than about 0.1 weight percent of the carbomer component.

Water has been viewed by the prior art to be necessary in order to have the paste in a smooth, flowable form. Its addition in bulk form, or in amounts that alter the flow characteristics, sheen, tackiness and viscosity of the gel/paste formulation of this invention, is prohibited. Most conventional dentifrices are composed of a matrix for the non-abrasive or non-filler ingredients, and that matrix is typically a water based homogeneous mixture. The dentifrice of this invention possesses an organic matrix which comprises a heterogeneous mixture of a continuous phase organic polyol and a discontinuous finely particulate amylopectin and/or acylated amylopectin phase. The much preferred formulation of the invention utilizes an acylated amylopectin phase. Dentifrices that rely on water and starch mixtures contain much of the water absorbed in the starch, causing the starch to be pasty and this results in particle to particle adhesion. In this invention, because water is not a material component of the formulation, the amylopectin and the acylated amylopectin particles are surrounded by the organic polyol, and that provides a slip surface for the individual particles and resulting in a high sheen composition which performs smoothly in cleaning teeth.

Flavoring agents are typically used in dentifrices. There is a substantial variety of them. They have nothing to do with the flow and cleansing characteristics of the dentifrice of this invention. They do make the dentifrice pleasant to taste and use. Cinnamon and mint are among the most popular flavors. Particular preference is given to a flavor such as that derived from the root of the *Glycyrrhiza glabra* plant or absinthe.

Foaming agents are often added to, but serve mainly to give a pleasant sensation, and apparently serve little or no cleaning purpose. Sodium lauryl sulfate, the one presently most frequently used, has generally replaced soap because there fewer compatibility problems in combining it with the other ingredients. However, cocamidopropyl betaine (CAS No. 61789-40-0; 83138-08-3; and 86438-79-1) can be used. Such foaming agents can be used in amounts ranging from about 0.5 to about 2.5 weight percent of the weight of the dentifrice formulation.

Sometimes preservative is added to prevent bacteria from forming in the dentifrice. This again is not an essential ingredient, but is one that is often desirable in the dentifrice formulation. In addition, such things as coloring agents may also be used.

A fluoridating agent may be incorporated, if desired, without harm to the other ingredients. The fluoridating agent may be, for example, sodium monofluorophosphate, sodium fluoride or stannous fluoride, in an amount of about 0.5 to about 1 weight percent of the formulation. It will have the same effect as fluorides have in other toothpastes when used, but will not affect at all the action on plaque, tartar, whitening or polishing. There is no evidence that fluoride in the formulation of the invention adversely affects the enzyme or peroxide content, nor is there any evidence that the enzyme and/or the hydrogen peroxide adversely effect the fluoride content or the stability of the fluoride. This stability is believed to derive from the essentially anhydrous nature of the formulation of this invention.

In a preferred embodiment, the formulation of the invention, if it employs an enzyme additive, it is desirable to incorporates alkali metal citrate in an amount of between about 1–3.5% of the total weight of the toothpaste. The preferred alkali metal citrates are sodium or potassium citrates or cesium citrate. Citric acid, an optional ingredient even when enzymes are added to the formation, may be used in combination therewith to about 3% by weight. It is used in an amount to adjust the pH somewhere between about 6.3 and about 7.6, all in view of the other ingredients contained. An approximation of 7.0 for the pH of the completed dentifrice is desirable.

If an enzyme is used (and it is preferably used), it may be incorporated in the amount of about 1 to about 10 weight percent. Based on experience, papain is the preferred enzyme, and desirably, as determined by the Milk Clot Assay Test of the Biddle-Sawyer Group, it an activity of 100–145 units per milligram. (See J. Biol. Chem., Volume 121, pages 737–745, (1937)). If papain, having a different activity, is used, it's concentration should be adjusted to an amount that corresponds to such values.

A Kitchen Aid, Heavy Duty Mixer, Model No. K5SS, with a stir setting (~65 rpm), and settings 2, 4, 6, 8 (~210 rpm) and 10 speed settings, and a flat beater mixing blade, was used to make the dentifrice gels/pastes in the mixing bowl, as characterized in the examples. It was determined that mixing sequence can be arbitrary without affecting the results so long as intimate mixing of the ingredients is achieved. All powdery components must be mixed in until they are thoroughly wetted and the formulation attains a creamy smooth paste or gel consistency. Because production economics of the product of the invention is dependent on rate of formation, it is desirable to rapidly mix the ingredients, typically whipping the components by operating the mixer at a high mixing speed, such as setting 8, which has been estimated to operate at about 210 rpm's. Whipping of the components appears not to stir air into the mix of this formulation but when water is used as an added ingredient, undesirable frothing of the mix has been noted. Because high speed mixing raises the temperature of the mix by as much as 20° C., it is desirable, when using high speed mixing, to not include the more volatile and heat sensitive materials in the mix at that stage of production and then to add such materials once the mixture has cooled to a safe (such as ambient room) temperature and continue mixing at a lower mixing speed so that the temperature in the mix does not similarly rise and the heat sensitive materials are not adversely affected. For this reason, it is desirable to add carbamide peroxide to the formulation after high speed mixing of the other formulation ingredients.

In the examples that follow, all percents are percent by weight of the final composition. Operating temperatures in which materials are mixed are ambient room temperature (—23.5° C.), and except where noted, temperature tracings of the mix was not taken during processing. All stirring in the examples is at stirrer setting except when stirring is raised to whipping at setting 8. All viscosities noted in the examples in cps (centipoises) are measured at 23.5° C. on a Brookfield Viscometer, Model DV-II, spindle 6, at 10 rpm's.

EXAMPLES

|  | Dentifrice #1 | Dentifrice #2 | Dentifrice #3 | Dentifrice #3A |
|---|---|---|---|---|
| Glycerine | 28.91% | 28.51% | 39.31% | 58.78% |
| COLFLO 67 ™* | 14.46% | 5.18% | 6.55% | 0 |
| National 4012 ™** | 7.23% | 6.92% | 3.90% | 0 |
| Urea hydrogen peroxide | 5.26% | 8.25% | 10.84% | 9.41% |
| Peppermint Flavoring | 2.63% | 0 | 0 | 0 |
| Mint flavor | 0 | 0 | 0.95% | 1.43% |
| Saccharin | 0 | 0 | 0.14% | 0.11% |
| Carbopol 940 | 0.07% | 0.05% | 0.62% | 0 |
| Sodium MFP | 2.12% | 0.63% | 1.01% | 1.53% |
| Papain | 0.95% | 0.27% | 0.39% | 0.29% |
| Sodium lauryl sulfate, 100% | 0.24% | 0 | 1.33% | 2.00% |
| Stepanol Wa-Extra (40 wt. % Sodium Lauryl Sulfate in water) | 0 | 0.97% | 0 | 0 |
| Sodium citrate | 7.97% | 2.35% | 3.12% | 4.70% |
| Hydrated alumina | 22.28% | 6.58% | 8.66% | 11.75% |
| Sylodent 573 | 7.89% | 40.29% | 23.17% | 0 |
| Aerosil 200 | 0 | 0 | 0 | 9.99% |

*National Food & Starch Co. Lot #CE9470
**National Food & Starch Co. Lot #CD4231

Preparation of Dentifrice #1:

1. Mix Glycerine, COLFLO, National 4012 and peroxide in the bowl at stirrer setting.
2. Add Carbopol to the bowl and mix for 30 minutes at stirrer setting.
3. Add and mix Na MFP, Papain, Stepanol, Na citrate and alumina.
4. Add Sylodent quickly and this caused the formulation to thicken too rapidly.

Preparation of Dentifrice #2:

1. Mix Glycerine, COLFLO, National 4012 and peroxide.
2. Add Carbopol and mix for 30 minutes.
3. Add and mix Na MFP, Papain, Stepanol, Na citrate and alumina.
4. Add Sylodent slowly and mix when completely added.
Observations: Too thick as a result of the high Sylodent concentration.

Preparation of Dentifrice #3:

1. Add Glycerine, COLFLO, Natn'l 4012, peroxide and Carbopol while mixing. Mix for 15 minutes at stirrer setting when done adding.
2. Add and mix Na MFP, Papain, SLS and Na citrate for 15 minutes.
3. Add and mix alumina for 10 minutes
4. Slowly add Sylodent and mix for 15 minutes.
5. Add flavor and saccharin and mix for 15 minutes.
Observation: Viscosity: 111,000 cps; creamy smooth flowing product.

Preparation of Dentifrice #3A:

1. Mix Glycerine and Aerosil for 30 minutes.
2. Add and mix remaining ingredients for 30 minutes.
Observation: Measures 7.87% carbamide peroxide.

|  | Dentifrice #4 | Dentifrice #5 | Dentifrice #6 | Dentifrice #7 |
|---|---|---|---|---|
| Glycerine | 42.55% | 42.55% | 42.55% | 42.55% |
| COLFLO 67* | 7.09% | 7.09% | 7.09% | 7.09% |
| National 4012** | 4.22% | 4.22% | 4.22% | 4.22% |
| Urea hydrogen peroxide | 3.50% | 3.50% | 3.50% | 3.50% |
| Mint flavor | 1.03% | 1.03% | 1.03% | 1.03% |
| Saccharin | 0.15% | 0.15% | 0.15% | 0.15% |
| Carbopol 940 | 0.68% | 0.68% | 0.68% | 0.68% |
| Sodium MFP | 1.10% | 1.10% | 1.10% | 1.10% |
| Papain | 0.42% | 0.42% | 0.42% | 4.78% |
| Sodium lauryl sulfate, 100% | 1.44% | 1.44% | 1.44% | 1.44% |

-continued

| | | | | |
|---|---|---|---|---|
| Sodium citrate | 3.38% | 3.38% | 3.38% | 3.38% |
| Hydrated alumina | 9.37% | 9.37% | 9.37% | 9.38% |
| Sylodent 573 | 25.07% | 25.07% | 25.07% | 25.07% |
| Aerosil 200 | 0 | 0 | 0 | 0 |

*National Food & Starch Co. Lot #CE9470
**National Food & Starch Co. Lot #CD4231

Preparation of Dentifrice #4:

1. Start with 50% Glycerine and add COLFLO, Natn'l 4012, Carbopol and Na citrate. Mix for 15 minutes at stir setting.
2. Add remaining 50% Glycerine and peroxide. Mix for 15 minutes at stir setting.
3. Add Na MFP, Papain and SLS. Mix for 15 minutes at stir setting.
4. Add flavor and saccharin. Mix for 15 minutes at stir setting.
5. Add alumina and Sylodent and mix for 15 minutes at stir setting.
Observations: Measures 3.16% carbamide peroxide.

Preparation of Dentifrice #5:

1. Mix all ingredients, except peroxide, for 45 minutes at stir setting.
2. Before cooling to room temperature, add peroxide and mix for another 15 minutes at stir setting.
Observations: Measures 3.09% peroxide.

Preparation of Dentifrice #6:

(COLFLO and Natn'l 4012 were each dried on a Moisture Balance-40% power for 15 min.)
1. Mix all ingredients, except peroxide, for 45 minutes at stir setting.
2. Before cooling to room temperature, add carbamide peroxide and mix for another 15 minutes at stir setting.
Observation: Measures 3.20% carbamide peroxide.

Preparation of Dentifrice #7:

1. Mix all ingredients, except carbamide peroxide, for 45 minutes at stir setting.
2. Without cooling to room temperature, add carbamide peroxide and mix for another 15 minutes at stir setting.
3. Whip formulation at setting 8 (210 rpm) for 25 minutes.
Observation: Measures 3.46% peroxide.

| | Dentifrice #8 | Dentifrice #9 | Dentifrice #10 | Dentifrice #11 |
|---|---|---|---|---|
| Glycerin | 42.32% | 41.11% | 41.11% | 41.11% |
| COLFLO 67* | 7.05% | 6.85% | 6.85% | 6.85% |
| National 4012** | 4.20% | 2.04% | 2.04% | 2.04% |
| Urea hydrogen peroxide | 3.48% | 3.38% | 3.38% | 3.38% |
| Mint flavor | 1.54% | 1.49% | 1.49% | 1.49% |
| Saccharin | 0.19% | 0.18% | 0.18% | 0.18% |
| Carbopol 940 | 0.67% | 0.65% | 0.65% | 0.65% |
| Sodium MFP | 1.09% | 1.06% | 1.06% | 1.06% |
| Papain | 0.42% | 0.41% | 0.41% | 0.41% |
| Sodium lauryl sulfate, 100% | 1.43% | 1.39% | 1.39% | 1.39% |
| Sodium citrate | 3.36% | 3.26% | 3.26% | 3.26% |
| Hydrated alumina | 9.32% | 9.05% | 9.05% | 9.05% |
| Sylodent 573 | 24.94% | 24.22% | 24.22% | 24.22% |
| Aerosil 200 | 0 | 4.89% | 4.89% | 4.89% |

*National Food & Starch Co. Lot #CE9470
**National Food & Starch Co. Lot #CD4231

Preparation of Dentifrice #8:

1. Mix all ingredients, except peroxide, for 45 minutes at stir setting.
2. Add peroxide and mix for another 15 minutes at stir setting.
3. Whip formulation on setting 8 (210 rpm) for 25 minutes.
Observations: Measures 3.42% peroxide Preparation of Dentifrice #9:

1. Mix Glycerine, COLFLO, Natn'l 4012, Carbopol, Na citrate, Na MFP, Papain, SLS, flavor, saccharin, alumina and Sylodent for 30 minutes at stir setting.
2. Slow intermittent additions of Aerosil followed by stirrer setting mixture, and after all Aerosil added, mix for 15 minutes at stirrer setting.
3. Add peroxide and mix for 15 minutes at stirrer setting.
4. Whip formulation on setting 8 for 25 minutes.
Observation: Measures 3.45% carbamide peroxide Preparation of Dentifrice #10:

1. Start with 50% of the Glycerine and add COLFLO, Natn'l 4012, Aerosil, Carbopol and Na citrate. Mix for 15 minutes at stirrer setting.
2. Add the remaining 50% Glycerine and peroxide. Mix for 15 minutes at stirrer setting.
3. Add Na MFP, Papain and SLS, flavor, saccharin, alumina and Sylodent. Mix for 15 minutes
4. Whip formulation on setting 8 for 25 minutes.
Observation: Measures 3.51% carbamide peroxide -continued Preparation of Dentifrice #11:

1. Mix Glycerine, COLFLO, Natn'l 4012, Carbopol, Na citrate, Na MFP, Papain, SLS, flavor,
   saccharin, alumina and Sylodent for 30 minutes at stirrer setting.
2. Slow intermittent additions of Aerosil followed by stirrer setting mixture, and after all Aerosil
   added, mix for 15 minutes at stirrer setting.
3. Whip on setting 8 for 25 minutes.
Let product cool to about room temperature

|  | Dentifrice #12 | Dentifrice #13 | Dentifrice #14 | Dentifrice #15 |
|---|---|---|---|---|
| Glycerin | 41.11% | 41.11% | 41.11% | 38.10% |
| COLFLO 67* | 6.85% | 6.85% | 6.85% | 6.85% |
| National 4012** | 2.04% | 2.04% | 2.04% | 2.04% |
| Urea hydrogen peroxide | 3.38% | 3.38% | 3.38% | 3.38% |
| Mint flavor | 0 | 0 | 0 | 0 |
| Sweet Mint Flavor | 1.49% | 0 | 1.49% | 1.49% |
| Bubblegum Flavor | 0 | 1.49% | 0 | 0 |
| Saccharin | 0.18% | 0.18% | 0.18% | 0.18% |
| Carbopol 940 | 0.65% | 0.65% | 0.65% | 0.65% |
| Sodium MFP | 1.06% | 1.06% | 1.06% | 1.06% |
| Papain | 0.41% | 0.41% | 0.41% | 0.41% |
| Sodium lauryl sulfate | 1.39% | 1.39% | 1.39% | 1.39% |
| Sodium citrate | 3.26% | 3.26% | 3.26% | 3.26% |
| Hydrated alumina | 9.05% | 9.05% | 9.05% | 9.05% |
| Sylodent 573 | 24.22% | 24.22% | 24.22% | 24.22% |
| Aerosil 200 | 4.89% | 4.89% | 4.89% | 4.89% |
| Propylene Glycol*** | 0 | 0 | 0 | 3.00% |

*National Food & Starch Co. Lot #CE9470
**National Food & Starch Co. Lot #CD4231
***Spectrum Mfg Chem Corp. Lot #KF066

Preparation of Dentifrice #12:

1. Mix Glycerine, COLFLO, Natn'l 4012, Carbopol, Na citrate, Na MFP, Papain, SLS, flavor, saccharin,
   alumina and Sylodent for 30 minutes at stirrer setting.
2. Slow intermittent additions of Aerosil followed by stirrer setting mixture, and after all Aerosil
   added, mix for 15 minutes at stirrer setting.
3. Whip on setting 8 for 25 minutes.
4. Add peroxide and mix for 15 minutes.
Observation: Measures 3.53% peroxide Preparation of Dentifrice #13:

1. Mix Glycerine, COLFLO, Natn'l 4012, Carbopol, Na citrate, Na MFP, Papain, SLS, flavor, saccharin,
   alumina and Sylodent for 30 minutes at stirrer setting.
2. Slow intermittent additions of Aerosil followed by stirrer setting mixture, and after all Aerosil
   added, mix for 15 minutes at stirrer setting.
3. Whip on setting 8 for 25 minutes.
4. Add peroxide and mix for 15 minutes.
Observation: Measures 3.75% peroxide Preparation of Dentifrice #14:

1. Mix Glycerine, COLFLO, Natn'l 4012, Carbopol, Na citrate, Na MFP, Papain, SLS, flavor, saccharin,
   alumina, and Sylodent for 30 minutes at stirrer setting.
2. Slow intermittent additions of Aerosil followed by stirrer setting mixture, and after all Aerosil
   added, mix for 15 minutes at stirrer setting.
3. Whip on setting 8 for 25 minutes.
4. Let product cool to Room Temperature.
5. Add peroxide and mix for 15 minutes.
Observations: Measures 3.53% peroxide and its viscosity measures 200,000 cps.

Preparation of Dentifrice #15:

1. Mix Glycerine, COLFLO, Natn'l 4012, Carbopol, Na citrate, Na MFP, Papain, SLS, flavor, saccharin,
   alumina, Sylodent and propylene glycol for 30 minutes.
2. Slow intermittent additions of Aerosil followed by stirrer setting mixture, and after all Aerosil
   added, mix for 15 minutes at stirrer setting.
3. Whip on setting 8 for 25 minutes.
4. Let product cool to Room Temperature.
5. Add peroxide and mix for 15 minutes.
Observations: Measures 3.79% peroxide, has a pH of 6.23 and a viscosity of 93,600 cps and a PAT
diameter viscosity of 9–10/16 inches.

|  | Dentifrice #16 | Dentifrice #17 | Dentifrice #18 | Dentifrice #18A | Dentifrice #19 |
|---|---|---|---|---|---|
| Glycerin | 41.26% | 42.51% | 38.25% | 38.45% | 38.25% |
| COLFLO 67* | 6.85% | 5.99% | 6.85% | 6.89% | 6.85% |
| National 4012** | 2.04% | 1.50% | 2.04% | 2.05% | 2.04% |
| Urea hydrogen peroxide | 3.38% | 3.38% | 3.38% | 3.40% | 3.38% |
| Mint Flavor | 1.49% | 1.49% | 1.49% | 1.50% | 1.49% |

-continued

| | | | | | |
|---|---|---|---|---|---|
| Saccharin | 0.18% | 0.18% | 0.18% | 0.18% | 0.18% |
| Carbopol 940 | 0.50% | 0.65% | 0.50% | 0 | 0.24% |
| Sodium MFF | 1.06% | 1.06% | 1.06% | 1.07% | 1.06% |
| Papain | 0.41% | 0.41% | 0.41% | 0.41% | 0.41% |
| Sodium lauryl sulfate | 1.39% | 1.39% | 1.39% | 1.40% | 1.39% |
| Sodium citrate | 3.26% | 3.26% | 3.26% | 3.28% | 3.26% |
| Hydrated alumina | 9.05% | 9.05% | 9.05% | 9.10% | 9.05% |
| Sylodent 573 | 24.22% | 24.22% | 24.22% | 24.35% | 24.22% |
| Aerosil 200 | 4.89% | 4.89% | 4.89% | 4.92% | 5.15% |
| Propylene Glycol*** | 0 | 0 | 3.00% | 3.02% | 3.00% |

*National Food & Starch Co. Lot #CE9470
**National Food & Starch Co. Lot #CD4231
***Spectrum Mfg Chem Corp. Lot #KF066

Preparation of Dentifrice #16:

1. Mix Glycerine, COLFLO, Natn'l 4012, Carbopol, Na citrate, Na MFP, Papain, SLS, flavor, saccharin, alumina and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes.

Observations: Measures 3.89% peroxide, pH 6.26 and a viscosity of 181,000 cps and a PAT diameter viscosity of 8.5–9.5/16"

Preparation of Dentifrice #17:

1. Mix Glycerine, COLFLO, Natn'l 4012, Carbopol, Na citrate, Na MFP, Papain, SLS, flavor, saccharin, alumina and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes.

Observations: Measures 4.12% peroxide, pH 5.85 and a viscosity of 147,000 cps and a PAT diameter viscosity of 9.5–10/16"

Preparation of Dentifrice #18:

1. Mix Glycerine, COLFLO, Natn'l 4012, Carbopol, Na citrate, Na MFP, Papain, SLS, flavor, saccharin, alumina, propylene glycol and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes.

Observations: Measures 4.02% peroxide, pH 5.92 and a viscosity of 114,000 cps (retested 119,000 cps) and a PAT diameter viscosity of 9–10/16"

Preparation of Dentifrice #18A:

1. Mix Glycerine, COLFLO, Natn'l 4012, Carbopol, Na citrate, Na MFP, Papain, SLS, flavor, saccharin, alumina, propylene glycol and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes Observations: Initial viscosity is 14,400 cps at room temperature. Heated in oven at 54.7° C. for 2 hours 16 minutes and re-measured viscosity, found to be 20,000 cps.

Preparation of Dentifrice #19:

1. Mix Glycerine, COLFLO, Natn'l 4012, Carbopol, Na citrate, Na MFP, Papain, SLS, flavor, saccharin, alumina, propylene glycol and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes.

Observations: Measures 4.07% peroxide, pH 6.38 and a viscosity of 85,600 cps and a PAT diameter viscosity of 10.5–10.5/16"

| | Dentifrice #20 | Dentifrice #21 | Dentifrice #22 | Dentifrice #23 | Dentifrice #24 |
|---|---|---|---|---|---|
| Glycerin | 41.52% | 37.41% | 38.06% | 19.13% | 38.25% |
| COLFLO 67* | 6.85% | 6.85% | 6.85% | 6.85% | 0 |
| National 4012** | 2.04% | 2.04% | 2.04% | 2.04% | 0 |
| Urea hydrogen peroxide | 3.38% | 3.38% | 3.38% | 3.38% | 8.89% |
| Sweet Mint Flavor | 1.49% | 1.49% | 0 | 1.49% | 3.38% |
| Mint flavor | 0 | 0 | 1.49% | 0 | 1.49% |

-continued

| | | | | | |
|---|---|---|---|---|---|
| Saccharin | 0.18% | 0.18% | 0.18% | 0.18% | 0.18% |
| Carbopol 940 | 0.24% | 0.24% | 0.44% | 0.50% | 0.50% |
| Sodium MFP | 1.06% | 1.06% | 1.06% | 1.06% | 1.06% |
| Papain | 0.41% | 0.41% | 0.41% | 0.41% | 0.41% |
| Sodium lauryl sulfate | 1.39% | 1.39% | 1.39% | 1.39% | 1.39% |
| Sodium citrate | 3.26% | 3.26% | 3.26% | 3.26% | 3.26% |
| Hydrated alumina | 9.05% | 9.05% | 9.05% | 9.05% | 9.05% |
| Sylodent 573 | 24.22% | 24.22% | 24.22% | 24.22% | 24.22% |
| Aerosil 200 | 4.89% | 5.99% | 5.15% | 4.89% | 4.89% |
| Propylene Glycol*** | 0 | 3.00% | 3.00% | 3.00% | 3.00% |
| Distilled Water | 0 | 0 | 0 | 19.13% | 0 |

*National Food & Starch Co. Lot #CE9470
**National Food & Starch Co. Lot #CD4231
***Spectrum Mfg Chem Corp. Lot #KF066

1. Preparation of Dentifrice #20:

2. Mix Glycerine, COLFLO, Natn'l 4012, Carbopol, Na citrate, Na MFP, Papain, SLS, flavor, saccharin, alumina and Sylodent for 30 minutes.
3. Slow intermittent additions of Aerosil followed by stirrer setting mixture, and after all Aerosil added, mix for 15 minutes at stirrer setting.
4. Whip on setting 8 for 25 minutes.
5. Let product cool to Room Temperature.
6. Add peroxide and mix for 15 minutes.

Observations: Measures 3.16% peroxide, pH 6.26 and a viscosity of 76,000 cps and a PAT diameter viscosity of 10–10/16"

Preparation of Dentifrice #21:

1. Mix Glycerine, COLFLO, Natn'l 4012, Carbopol, Na citrate, Na MFP, Papain, SLS, flavor, saccharin, alumina, propylene glycol and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes.

Observations: Measures 3.95% peroxide, pH 6.37 and a viscosity of 76,000 cps and a PAT diameter viscosity of 10.5–10.5/16"

Preparation of Dentifrice #22:

1. Mix Glycerine, COLFLO, Natn'l 4012, Carbopol, Na citrate, Na MFP, Papain, SLS, flavor, saccharin, alumina, propylene glycol and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes.

Observations: Measures 4.03% peroxide, pH 6.25 and a viscosity of 56,000 cps and a PAT diameter viscosity of 11–12/16"

Preparation of Dentifrice #23:

1. Mix Glycerine, COLFLO, Natn'l 4012, Carbopol, Na citrate, Na MFP, Papain, SLS, flavor, saccharin, alumina, propylene glycol, water and Sylodent for 30 minutes.
2. Slow intermittent additions of Aerosil followed by stirrer setting mixture, and after all Aerosil added, mix for 15 minutes at stirrer setting.
3. Whip on setting 8 for 25 minutes and noted that the mass became frothy.
4. Let product cool to Room Temperature and the froth collapsed.
5. Add peroxide and mix for 15 minutes.

Observations: Measures 4.05% peroxide, pH 6.18 and a viscosity of 308,000 cps (retested 294,000 cps) and a PAT diameter viscosity of 6–6/16"

Preparation of Dentifrice #24:

1. Mix Glycerine, cornstarch, Carbopol, Na citrate, Na MFP, Papain, SLS, flavor, saccharin, alumina and Sylodent for 30 minutes
2. Slow intermittent additions of Aerosil followed by stirrer setting mixture, and after all Aerosil added, mix for 15 minutes at stirrer setting.
3. Whip on setting 8 for 25 minutes.
4. Let product cool to Room Temperature.
5. Add peroxide and mix for 15 minutes.

Observations: Measures 4.30% peroxide, pH 6.45 and a viscosity of 60,800 cps and a PAT diameter viscosity of 11.5–12.5/16"

The following examples, nos. 25–30, using the procedures described above, depict bleaching and brushing gel formulations embodying the invention.

|  | Bleaching Gel (#25) | Bleaching Gel (#26) | Bleaching Gel (#27) | Bleaching Gel (#28) | Bleaching Gel (#29) | Brushing Gel (#30) |
| --- | --- | --- | --- | --- | --- | --- |
| Glycerin | 55.37% | 52.49% | 46.90% | 35.00% | 54.31% | 52.52% |
| COLFLO 67 | 11.40% | 10.41% | 9.64% | 7.33% | 11.40% | 10.41% |
| National 4012 | 4.09% | 3.09% | 2.87% | 2.76% | 4.08% | 3.09% |
| Urea hydrogen peroxide | 10.00% | 15.00% | 22.00% | 35.00% | 10.00% | 5.00% |
| Sweet Mint Flavor | 1.49% | 1.49% | 1.49% | 1.49% | 1.49% | 1.49% |
| Saccharin | 0.18% | 0.18% | 0.18% | 0.18% | 0.18% | 0.18% |
| Carbopol 940 | 0.50% | 0.50% | 0.50% | 0.50% | 0.50% | 0.50% |
| Sodium MFP | 0 | 0 | 0 | 0 | 1.06% | 1.06% |
| Papain | 0 | 0 | 0 | 0 | 0 | 0.41% |
| Sodium lauryl sulfate | 0 | 0 | 0 | 0 | 0 | 1.39% |
| Sodium citrate | 4.00% | 5.20% | 7.50% | 12.00% | 4.00% | 3.26% |
| Hydrated alumina | 0 | 0 | 0 | 0 | 0 | 9.05% |
| Aerosil 200 | 8.42% | 7.42% | 6.86% | 4.52% | 8.42% | 7.42% |
| Propylene Glycol | 4.55% | 4.22% | 2.06% | 2.77% | 4.55% | 4.22% |

A particularly preferred formulation is set forth in example 31.

EXAMPLE 31

| INGREDIENTS | PERCENT BY WEIGHT |
| --- | --- |
| Glycerine | 34.35 |
| Propylene Glycol 3.02% | 2.01 |
| Carbopol 940 | 0.48 |
| Sodium Citrate | 3.26 |
| Saccharin | 0.18 |
| Sodium Monofluorophosphate (MFP) | 1.05 |
| National 4012 (National Starch) | 1.90 |
| Colflo 67 (National Starch) | 6.69 |
| Sylodent 573 | 24.16 |
| Aerosil 200 | 4.12 |
| Hydrated Aluminum Oxide | 9.03 |
| Papain | 0.80 |
| Urea hydrogen peroxide | 9.10 |
| Sodium lauryl sulfate | 1.38 |
| Wintergreen flavor | 1.49 |
| Total | 100 |

This formulation was made by combining the ingredients in a mixer that contains a cylindrical vacuum tank containing an "anchor" blade. The anchor blade is a relatively slow-moving blade, which fits closely to the tank wall and bottom. The blade usually has attached Teflon® followers that actually scrape the walls and bottom of the tank. The tank also contains a disperser blade. The disperser blade is a relatively fast-moving blade possessing a disk with peripheral vertical blades. The disperser blade is positioned inside the swept area of the anchor blade and is of much smaller diameter. Both blades are designed for variable speed. Typical speed ranges are 20–200 rpm for the anchor blade, more typically from about 20 to about 100 rpm, and 100–5000 rpm for the disperser. The mix tank is fitted with a cooling jacket. Typical of such a mixer is the Premier ESD2017,5, the Myers V550A-15-25-d115, and the Ross PVM-500.

Mixing procedure for the above formulation of this example is as follows:
1) In a Premier 100-gal mixer, add 16.1 weight % of the formulation weight, of glycerine, all of the propylene glycol, and the Carbopol. Set the anchor blade at 45 rpm, the disperser at 1450 rpm and mix until the Carbopol is dispersed.

2) Add the sodium citrate and continue mixing until all of the ingredients are dissolved. Do not let temperature exceed 190° F.

3) Pump above mix into a Ross 500-gal mixer. Add 14.6 weight % of the formulation weight, of glycerine and start cooling via the cooling jacket. Then the disperser is set at 3500–4500 rpm and anchor at 85–100 rpm. Add the sodium saccharine to the open hatch of the mixer with continuous mixing, add MFP with continued mixing, and then vacuum load National 4012, Colflo 67, and the Sylodent 573. The vacuum is broken and the remaining quantity of glycerine is top loaded to the formulation in the tank. Then the Aerosil 200 and hydrated Aluminum Oxide are vacuum loaded to the tank. The batch is then cooled to 105° F.–110° F., followed by top load addition of the papain, peroxide, sodium lauryl sulfate and flavor, in that order. Mixing is continued for about 5–7 minutes until the product is homogenous; then mixing is stopped and the tank bowl and blades are scraped clean. Mixing is then resumed under vacuum to de-aerate for 25–30 minutes. Total mix time, including time for addition of ingredients, is approximately six hours.

We claim:

1. A bulk-water-free dentifrice comprising a stable mixture of at least one of amylopectin containing discrete solid particles and modified amylopectin containing discrete solid particles, suspended in a liquid matrix material.

2. A thixotropic, smooth-flowing liquid, bulk-water-free dentifrice gel/paste that contains a stable mixture of at least one of amylopectin containing discrete solid particles and modified amylopectin containing discrete solid particles, uniformly suspended in and wetted by an inert essentially anhydrous organic hydroxylated liquid matrix material, and which dentifrice gel/paste is characterized by a high surface sheen.

3. The thixotropic, smooth flowing liquid, bulk-water free dentifrice gel/paste of claim 2 wherein the modified homopolysachharide discrete particles contain esterified amylopectin and/or esterified amylose.

4. The thixotropic, smooth flowing liquid, bulk-water-free dentifrice gel/paste of claim 2 wherein the dentifrice gel/paste forms a sticky and tacky film on teeth that withstands nonaqueous rubbing with a toothbrush, but which will incrementally disperse on contact with water and saliva.

5. The thixotropic, smooth flowing liquid, bulk-water-free dentifrice gel/paste of claim 2 wherein the dentifrice gel/paste extrudes from a tube or syringe orifice opening as a stable creamy fluid having an uniform viscosity, that is cleanly, without forming a sticky mess on a surface at the orifice opening, a patients hands, a brush handle, and a dental tray, cleaved like soft, non-fluid butter, and neatly deposited on another surface.

6. The thixotropic, smooth flowing liquid, bulk-water-free dentifrice gel/paste of claim 2 wherein the dentifrice gel/paste contains a flavoring additive.

7. The thixotropic, smooth flowing liquid, bulk-water-free dentifrice gel/paste of claim 2 wherein the dentifrice gel/paste maintains its creamy flowable viscosity over extended periods of time, even when heated at temperatures as high as 40° C..

8. The thixotropic, smooth flowing liquid, bulk-water-free dentifrice gel/paste of claim 2 wherein the surface of the dentifrice gel/paste exhibits glistening brightness and luster.

9. The thixotropic, smooth flowing liquid, bulk-water-free dentifrice gel/paste of claim 8 wherein the dispersed solids in the dentifrice gel/paste are coated by a distinct liquid phase that contributes a sheen to the product.

10. The thixotropic, smooth flowing liquid, bulk-water-free dentifrice gel/paste of claim 9 wherein the dentifrice gel/paste is a heterogeneous uniform mixture of at least two phases, one phase being a liquid continuous phase comprising the essentially anhydrous organic hydroxylated liquid matrix material, and another phase comprising fine particles containing solid particles of acylated amylopectin.

11. The thixotropic, smooth flowing liquid, bulk-water-free dentifrice gel/paste of claim 10 wherein the dentifrice gel/paste has a stable viscous creamy texture when extruded from a tube or syringe orifice, and when deposited on a surface, the dentifrice gel/paste retains the creamy characteristic.

12. The thixotropic, smooth flowing liquid, bulk-water-free dentifrice gel/paste of claim 10 wherein the dentifrice gel/paste, without added pigmentation or colorant, when spread over a solid surface, forms a glistening and tacky withe-opaque film that significantly bonds to the surface, and is not easily wiped away from the surface.

13. The thixotropic, smooth flowing liquid, bulk-water-free dentifrice gel/paste of claim 10 wherein the dentifrice gel/paste clings to teeth enamel surfaces to which it is applied in the absence of added water and/or saliva.

14. The thixotropic, smooth flowing liquid, bulk-water-free dentifrice gel/paste of claim 2 wherein the organic hydroxylated liquid matrix material is one or more liquids which remain liquid at temperatures as low as about 0° C., or lower, to as high as about 290° C., or higher, as determined at atmosphere pressure.

15. The thixotropic, smooth flowing liquid, bulk-water free dentifrice gel/paste of claim 14 wherein the organic hydroxylated liquid matrix material is one or more aliphatic organic polyols.

16. The thixotropic, smooth flowing liquid, bulk-water free dentifrice gel/paste of claim 10 wherein the organic hydroxylated liquid matrix material is one or more of glycerine and propylene glycols of the formula:

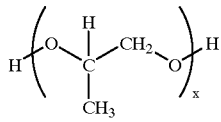

wherein x has a value of 1 to about 5.

17. The thixotropic, smooth liquid, bulk-water-free dentifrice gel/paste of claim 16 wherein the organic hydroxylated liquid matrix material is from the group consisting fo glycerine, 1,2-propylene glycol and mixtures thereof.

18. The thixotropic, smooth flowing liquid, bulk-water-free dentifrice gel/paste of claim 2 wherein the dentifrice gel/paste includes a small quanity of high molecular weight acidic polymer.

19. The thixotropic, smooth flowing liquid, bulk-water-free dentifrice gel/paste of claim 18 wherein the acidic polymer is a carboxylated polymer or silica.

20. The thixotropic, smooth liquid, bulk-water-free dentifrice gel/paste of claim 19 wherein the acidic polymer is a carbomer.

21. The thixotropic, smooth flowing liquid, bulk-water-free dentifrice gel/paste of claim 10 wherein the dentifrice gel/paste comprises the admixture of a limited quantity of granulated, finely and uniformly dispersed, esterified amylopectin and/or esterfied amylose with a relatively small amount of a powered carbomer polymer, both in an essentially anhydrous hydroxylated organic liquid matrix material that wets each component and allows the formation of the gelled state.

22. The thixotropic, smooth flowing liquid, bulk-water-free dentifrice gel/paste of claim 21 wherein the amount of esterified amylopectin and/or esterified amylose by weight in the dentifrice gel exceed the weight amount of the carbomer polymer, and the weight amount of the matrix material exceeds the weight of both the esterified amylose pectin and/or esterified amylose and the carbomer polymer.

23. The thixotropic, smooth flowing liquid, bulk-water-free dentifrice of claim 21 wherein the dentifrice gel/paste contains at least one of a whitener, brightener, and fluoride.

24. The thixotropic, smooth flowing liquid, bulk-water-free dentifrice gel/paste of claim 22 wherein dentifrice gel/paste has a viscosity ranging from about 50,000 to about 200,000 centipoise when measured at 23.5° C. on a Brookfield Viscometer, Model DV-II, spindle 6, at 10 rpm's.

25. The thixotropic, smooth flowing liquid, bulk-water-free dentifrice gel/paste of claim 24 wherein the viscosity is in the range of about 65,000 to about 180,000 centipoise.

26. The thixotropic, smooth flowing liquid, bulk-water-free dentifrice gel/paste of claim 24 wherein the viscosity is in the range of about 75,000 to about 150,000 centipoise.

27. The thixotropic, smooth flowing liquid, bulk-water-free dentifrice gel/paste of claim 23 wherein dentifrice gel/paste contains carbamide peroxide.

28. The thixotropic, smooth flowing liquid, bulk-water-free dentifrice gel/paste of claim 23 wherein dentifrice gel/paste contains sodium MFP.

29. The thixotropic, smooth flowing liquid, bulk-water-free dentifrice gel/paste of claim 27 wherein dentifrice gel/paste contains sodium MFP.

30. The thixotropic, smooth flowing liquid, bulk-water-free dentifrice gel/paste of claim 23 wherein dentifrice gel/paste contains an enzyme.

31. The thixotropic, smooth flowing liquid, bulk-water-free dentifrice gel/paste of claim 30 wherein dentifrice gel/paste contains papain.

32. The thixotropic, smooth flowing liquid, bulk-water-free dentifrice gel/paste of claim 31 wherein dentifrice gel/paste contains an alkali metal citrate.

33. The thixotropic, smooth flowing liquid, bulk-water-free dentifrice gel/paste of claim 32 wherein the citrate is one or more of sodium and potassium citrate.

34. The thixotropic, smooth flowing liquid, bulk-water-free dentifrice gel/paste of claim 2 wherein dentifrice gel/paste contains an abrasive.

35. The thixotropic, smooth flowing liquid, bulk-water-free dentifrice gel/paste of claim 34 wherein the abrasive is an aluminum oxide.

36. The thixotropic, smooth flowing liquid, bulk-water-free dentifrice gel/paste of claim 34 wherein the abrasive is a silicon oxide.

37. The thixotropic, smooth flowing liquid, bulk-water-free dentifrice gel/paste of claim 34 wherein the abrasive is a mixture of aluminum oxide and silicon oxide abrasives.

38. A method of whitening teeth in which teeth are subjected to a peroxide by placing a bleach gel in a dental tray and placing the dental tray over the teeth whereby the teeth are in contact with the bleaching gel, the improvement which comprises using as the bleaching gel the dentifrice gel/paste of claim 27.

* * * * *

UNITED STATES PATENT AND TRADEMARK OFFICE
CERTIFICATE OF CORRECTION

PATENT NO. : 6,331,291 B1
DATED : December 18, 2001
INVENTOR(S) : Glace, William R. et al.

It is certified that error appears in the above-identified patent and that said Letters Patent is hereby corrected as shown below:

<u>Title page,</u>
Assignee, Den-Mat Corporation, Santa Maria, California, USA <u>Column 2,</u>
Line 27, replace "it is difficult o force ..." with -- it is difficult to force --

<u>Column 3,</u>
Line 57, replace "he second is that..." with -- The second is that --

<u>Column 5,</u>
Lines 55-60, replace

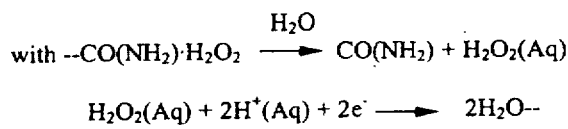

$$"CO(NH_2) \cdot H_2O_2 \xrightarrow{H_2O} CO(NH_2) + H_2O_2(Aq)$$

$$H_2O_2(Aq) + 2H^+(Aq) + 2e^- \longrightarrow 2H_2O"$$

with 
$$--CO(NH_2) \cdot H_2O_2 \xrightarrow{H_2O} CO(NH_2) + H_2O_2(Aq)$$

$$H_2O_2(Aq) + 2H^+(Aq) + 2e^- \longrightarrow 2H_2O--$$

<u>Column 6,</u>
Line 5, replace "corn. potatoes,..." with -- corn, potatoes --

<u>Column 7,</u>
Lines 16-17, replace "such as protecting cells, malonic acid,..." with -- such as.malonic acid --
Line 28, replace "an preferably at least..." with -- and preferably at least --

<u>Column 13,</u>
Line 62, replace "as if a sharpened knife-edge=is..." with -- as if a sharpened knife-edge is --

UNITED STATES PATENT AND TRADEMARK OFFICE
CERTIFICATE OF CORRECTION

PATENT NO. : 6,331,291 B1
DATED : December 18, 2001
INVENTOR(S) : Glace, William R. et al.

It is certified that error appears in the above-identified patent and that said Letters Patent is hereby corrected as shown below:

<u>Column 24,</u>
Line 4, replace "(--23.5°C.)" with -- (23.5°C.) --

Signed and Sealed this

Twenty-first Day of May, 2002

Attest:

JAMES E. ROGAN
*Attesting Officer*     *Director of the United States Patent and Trademark Office*